US012690781B2

(12) United States Patent　(10) Patent No.:　US 12,690,781 B2
Salter et al.　(45) Date of Patent:　Jul. 28, 2026

(54) METHOD AND DEVICE FOR TIERED POSTURE AWARENESS

(71) Applicant: Apple Inc., Cupertino, CA (US)

(72) Inventors: Thomas G. Salter, Foster City, CA (US); Adeeti V. Ullal, Los Altos, CA (US); Alexander G. Bruno, Cupertino, CA (US); Daniel M. Trietsch, San Jose, CA (US); Edith M. Arnold, Redwood City, CA (US); Edwin Iskandar, San Jose, CA (US); Ioana Negoita, San Jose, CA (US); James J. Dunne, San Francisco, CA (US); Johahn Y. Leung, San Francisco, CA (US); Karthik Jayaraman Raghuram, Frederick, MD (US); Matthew S. DeMers, Lexington, KY (US); Thomas J. Moore, Northglenn, CO (US)

(73) Assignee: Apple Inc., Cupertino, CA (US)

( * ) Notice: Subject to any disclaimer, the term of this patent is extended or adjusted under 35 U.S.C. 154(b) by 469 days.

(21) Appl. No.: 18/200,545

(22) Filed: May 22, 2023

(65) Prior Publication Data

US 2024/0023830 A1　Jan. 25, 2024

Related U.S. Application Data

(60) Provisional application No. 63/344,729, filed on May 23, 2022.

(51) Int. Cl.
A61B 5/11　　(2006.01)
G06F 3/01　　(2006.01)

(52) U.S. Cl.
CPC ........... *A61B 5/1107* (2013.01); *A61B 5/1116* (2013.01); *G06F 3/012* (2013.01)

(58) Field of Classification Search
CPC ..... A61B 5/1107; A61B 5/1116; G06F 3/012; G06F 3/011; G06T 2207/30196;
(Continued)

(56) References Cited

U.S. PATENT DOCUMENTS 10,682,093 B1　6/2020　Stein et al.
2012/0190998 A1 *　7/2012　Armitstead ....... A61M 16/0633
128/204.23
(Continued)

FOREIGN PATENT DOCUMENTS

WO　　2020054954 A1　3/2020

*Primary Examiner* — Patrick Fernandes
(74) *Attorney, Agent, or Firm* — Fernando & Partners, LLP

(57)　　ABSTRACT

In one implementation, a method is performed for tiered posture awareness. The method includes: while presenting a three-dimensional (3D) environment, via the display device, obtaining head pose information for a user associated with the computing system; determining an accumulated strain value for the user based on the head pose information; and in accordance with a determination that the accumulated strain value for the user exceeds a first posture awareness threshold: determining a location for virtual content based on a height value associated with the user and a depth value associated with the 3D environment; and presenting, via the display device, the virtual content at the determined location while continuing to present the 3D environment via the display device.

20 Claims, 17 Drawing Sheets

(58) Field of Classification Search
     CPC ..... G06T 2210/41; G06T 19/006; G06T 7/73;
              G16H 20/30; G16H 40/63; G16H 50/30
     See application file for complete search history.

(56)                    References Cited

U.S. PATENT DOCUMENTS

| 2019/0130622 | A1* | 5/2019 | Hoover | G06F 3/012 |
| 2019/0272772 | A1 | 9/2019 | Wexler et al. | |
| 2020/0135324 | A1 | 4/2020 | Roy et al. | |
| 2023/0296884 | A1* | 9/2023 | Robbins | G06F 3/012 |
| | | | | 345/8 |

* cited by examiner

Figure 2:
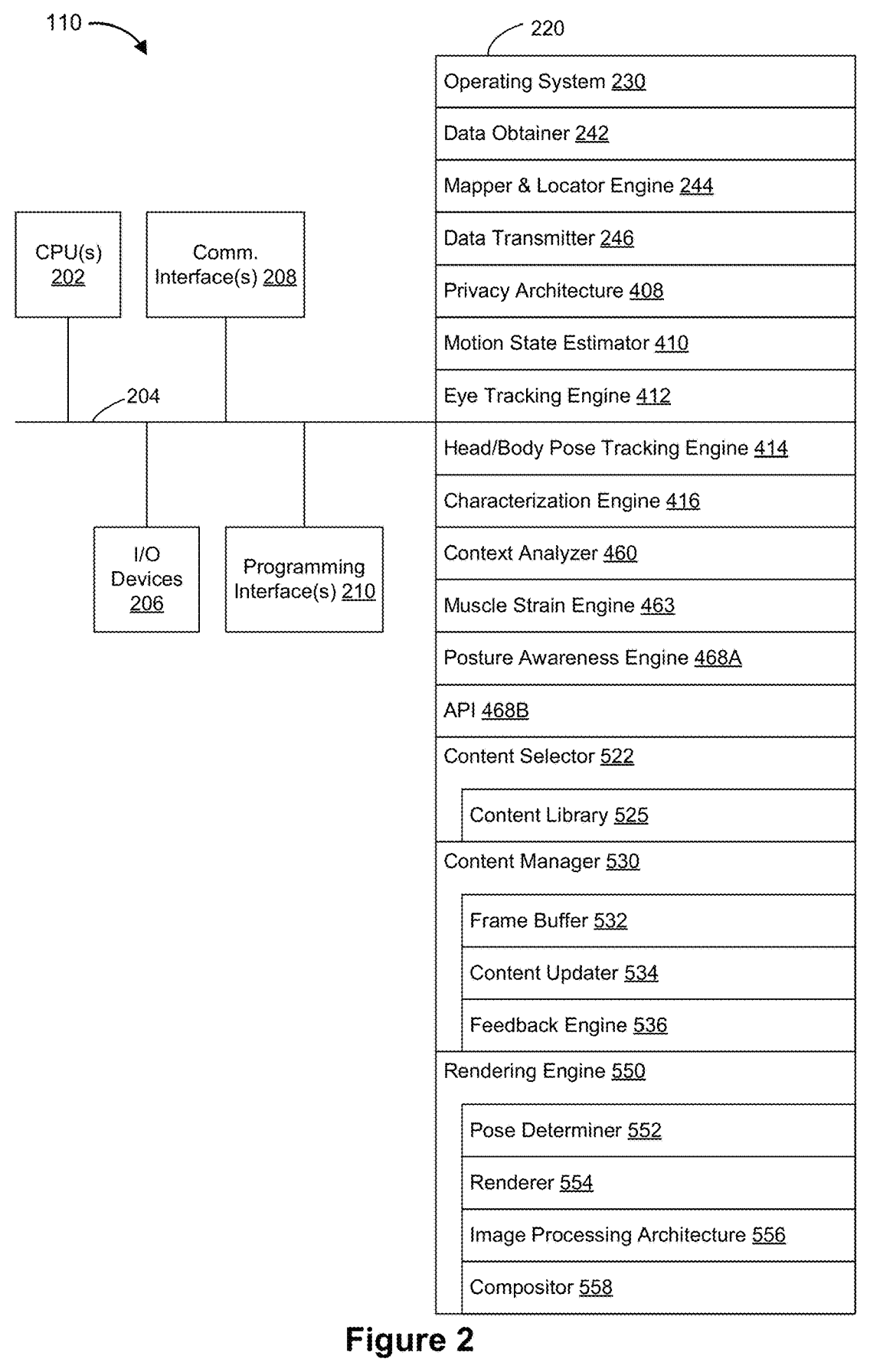

110 ⟍

220

| Operating System 230 |
| --- |
| Data Obtainer 242 |
| Mapper & Locator Engine 244 |
| Data Transmitter 246 |
| Privacy Architecture 408 |
| Motion State Estimator 410 |
| Eye Tracking Engine 412 |
| Head/Body Pose Tracking Engine 414 |
| Characterization Engine 416 |
| Context Analyzer 460 |
| Muscle Strain Engine 463 |
| Posture Awareness Engine 468A |
| API 468B |
| Content Selector 522 |

| CPU(s) 202 | Comm. Interface(s) 208 |
| --- | --- |

204

| I/O Devices 206 | Programming Interface(s) 210 |
| --- | --- |

Content Selector 522

> Content Library 525

Content Manager 530

> Frame Buffer 532
>
> Content Updater 534
>
> Feedback Engine 536

Rendering Engine 550

> Pose Determiner 552
>
> Renderer 554
>
> Image Processing Architecture 556
>
> Compositor 558

Figure 4B:
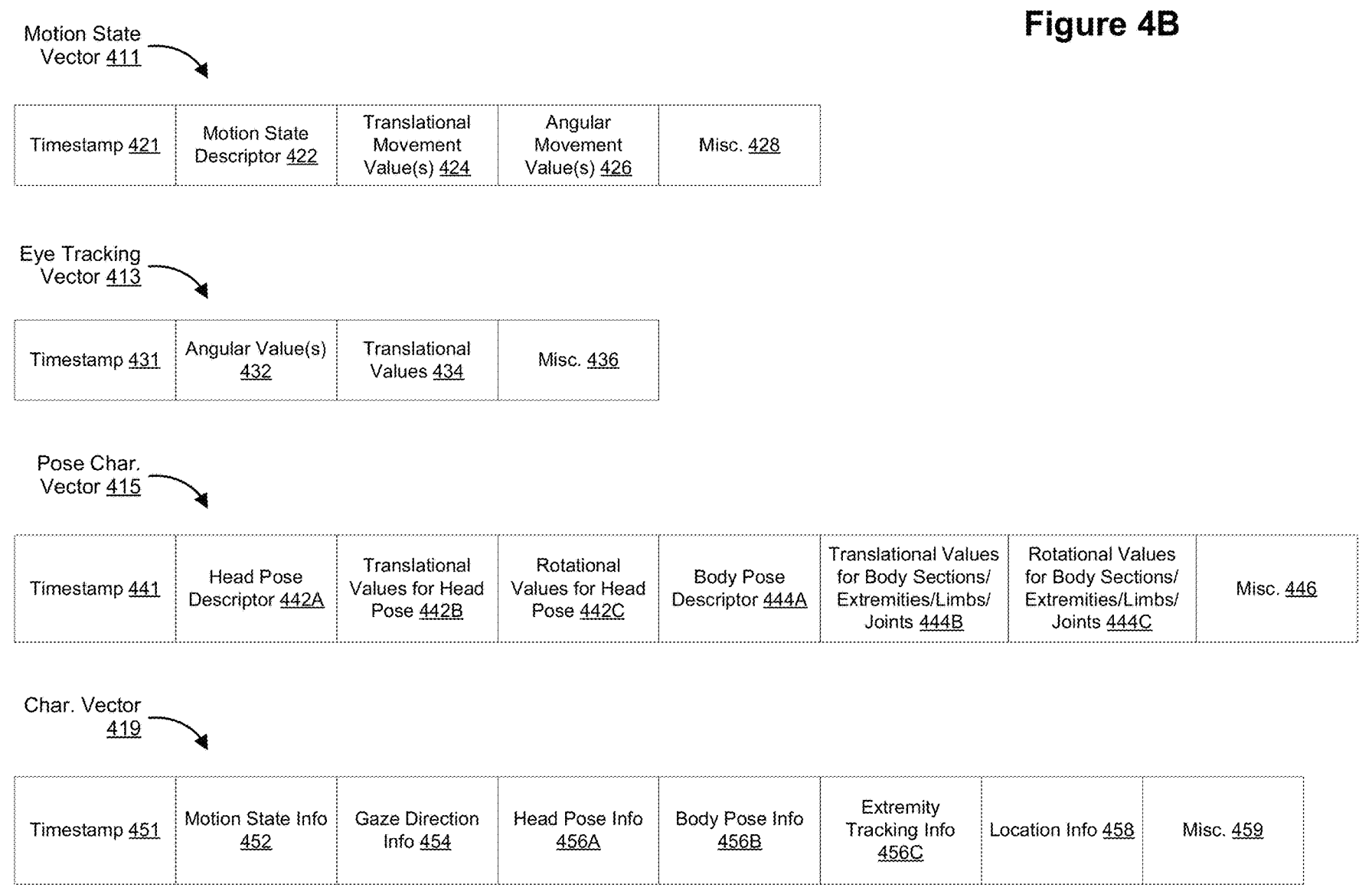

Motion State Vector 411

| Timestamp 421 | Motion State Descriptor 422 | Translational Movement Value(s) 424 | Angular Movement Value(s) 426 | Misc. 428 |

Eye Tracking Vector 413

| Timestamp 431 | Angular Value(s) 432 | Translational Values 434 | Misc. 436 |

Pose Char. Vector 415

| Timestamp 441 | Head Pose Descriptor 442A | Translational Values for Head Pose 442B | Rotational Values for Head Pose 442C | Body Pose Descriptor 444A | Translational Values for Body Sections/ Extremities/Limbs/ Joints 444B | Rotational Values for Body Sections/ Extremities/Limbs/ Joints 444C | Misc. 446 |

Char. Vector 419

| Timestamp 451 | Motion State Info 452 | Gaze Direction Info 454 | Head Pose Info 456A | Body Pose Info 456B | Extremity Tracking Info 456C | Location Info 458 | Misc. 459 |

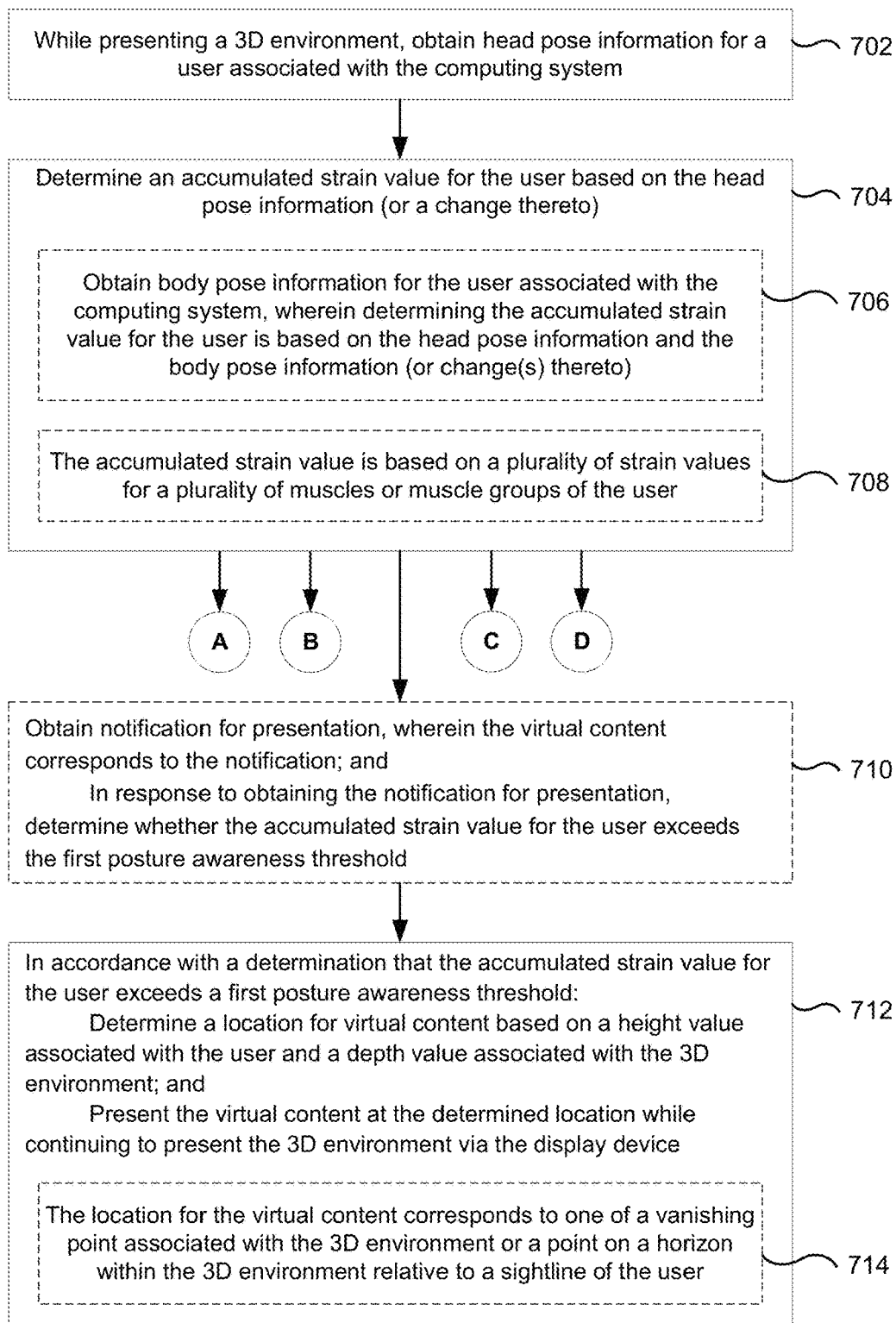

700

While presenting a 3D environment, obtain head pose information for a user associated with the computing system — 702

Determine an accumulated strain value for the user based on the head pose information (or a change thereto) — 704

Obtain body pose information for the user associated with the computing system, wherein determining the accumulated strain value for the user is based on the head pose information and the body pose information (or change(s) thereto) — 706

The accumulated strain value is based on a plurality of strain values for a plurality of muscles or muscle groups of the user — 708

A   B    C   D

Obtain notification for presentation, wherein the virtual content corresponds to the notification; and
    In response to obtaining the notification for presentation, determine whether the accumulated strain value for the user exceeds the first posture awareness threshold — 710

In accordance with a determination that the accumulated strain value for the user exceeds a first posture awareness threshold:
    Determine a location for virtual content based on a height value associated with the user and a depth value associated with the 3D environment; and
    Present the virtual content at the determined location while continuing to present the 3D environment via the display device — 712

The location for the virtual content corresponds to one of a vanishing point associated with the 3D environment or a point on a horizon within the 3D environment relative to a sightline of the user — 714

Figure 7A

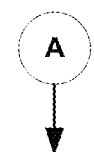

In accordance with a determination that the accumulated strain value for the user does not exceed the first posture awareness threshold, maintain presentation of the 3D environment and forgoing presentation of the virtual content at the determined location ⌐∼ 716

In accordance with a determination that the accumulated strain value for the user exceeds a second posture awareness threshold greater than the first posture awareness threshold, change an appearance of at least a portion of at least one edge of the display device ⌐∼ 718

Changing the appearance of at least the portion of at least the one edge of the display device corresponds to peripheral lighting or a peripheral glow effect ⌐∼ 720

In accordance with a determination that the accumulated strain value for the user exceeds a second posture awareness threshold greater than the first posture awareness threshold, provide spatial audio relative to at least one auditory edge of the user ⌐∼ 722

Figure 7B

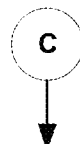

In accordance with a determination that the accumulated strain value for the user exceeds a third posture awareness threshold greater than the second posture awareness threshold, present second virtual content within the 3D environment, wherein the second virtual content corresponds to an alert notification indicating that the user has been overstaining one or more muscles or muscle groups ⟿ 724

In accordance with a determination that the accumulated strain value for the user exceeds a fourth posture awareness threshold greater than the third posture awareness threshold, present an affordance within the 3D environment, wherein the affordance enables the user to initiate a stretching session to ameliorate the accumulated strain value ⟿ 726

Figure 7C

METHOD AND DEVICE FOR TIERED POSTURE AWARENESS

CROSS-REFERENCE TO RELATED APPLICATIONS

This application is claims priority to U.S. Provisional Patent App. No. 63/344,729, filed on May 23, 2022, which is hereby incorporated by reference in its entirety.

TECHNICAL FIELD

The present disclosure generally relates to posture awareness and, in particular, to systems, devices, and methods for tiered posture awareness.

BACKGROUND

Many persons may spend a significant number of hours at their computers or other devices during both work and non-work hours. This time spent using a computer or other devices may negatively impact the posture of said person.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIG. 2 is a block diagram of an example controller in accordance with some implementations.

FIG. 4B illustrates example data structures in accordance with some implementations.

FIGS. 7A-7C illustrate a flowchart representation of a method of presenting tiered posture awareness in accordance with some implementations.

Figure 1:
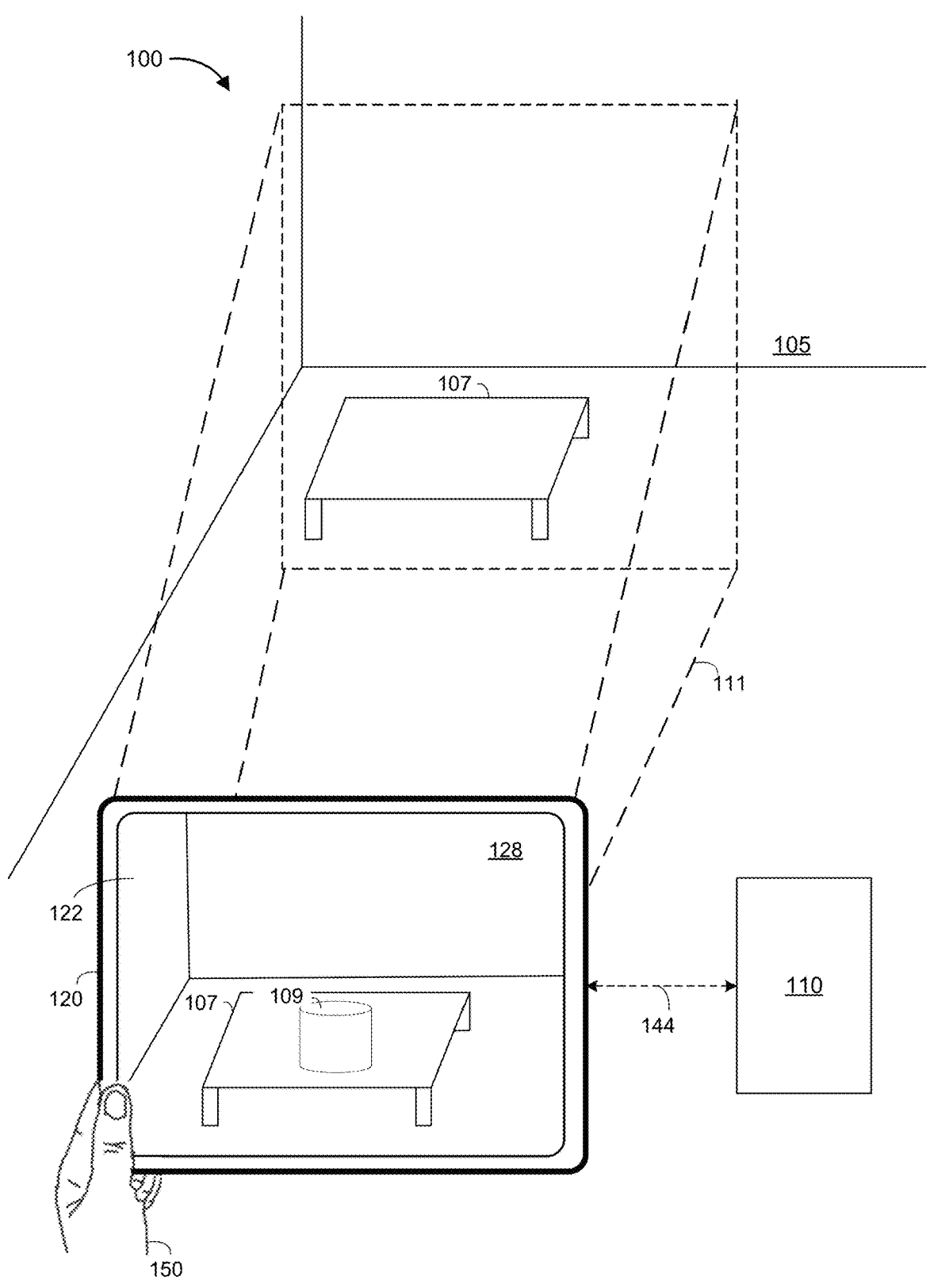
FIG. 1 is a block diagram of an example operating architecture in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

SUMMARY

Various implementations disclosed herein include devices, systems, and methods for tiered posture awareness.

According to some implementations, the method is performed at a computing system including non-transitory memory and one or more processors, wherein the computing system is communicatively coupled to a display device and one or more input devices. The method includes: while presenting a three-dimensional (3D) environment, via the display device, obtaining head pose information for a user associated with the computing system; determining an accumulated strain value for the user based on the head pose information; and in accordance with a determination that the accumulated strain value for the user exceeds a first posture awareness threshold: determining a location for virtual content based on a height value associated with the user and a depth value associated with the 3D environment; and presenting, via the display device, the virtual content at the determined location while continuing to present the 3D environment via the display device.

In accordance with some implementations, an electronic device includes one or more displays, one or more processors, a non-transitory memory, and one or more programs; the one or more programs are stored in the non-transitory memory and configured to be executed by the one or more processors and the one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more displays, one or more processors, a non-transitory memory, and means for performing or causing performance of any of the methods described herein.

In accordance with some implementations, a computing system includes one or more processors, non-transitory memory, an interface for communicating with a display device and one or more input devices, and one or more programs; the one or more programs are stored in the non-transitory memory and configured to be executed by the one or more processors and the one or more programs include instructions for performing or causing performance of the operations of any of the methods described herein. In accordance with some implementations, a non-transitory computer readable storage medium has stored therein instructions which when executed by one or more processors of a computing system with an interface for communicating with a display device and one or more input devices, cause the computing system to perform or cause performance of the operations of any of the methods described herein. In accordance with some implementations, a computing system includes one or more processors, non-transitory memory, an interface for communicating with a display device and one or more input devices, and means for performing or causing performance of the operations of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

FIG. 1 is a block diagram of an example operating architecture 100 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating architecture 100 includes an optional controller 110 and an electronic device 120 (e.g., a tablet, mobile phone, laptop, near-eye system, wearable computing device, or the like).

In some implementations, the controller 110 is configured to manage and coordinate an extended reality (XR) experience (sometimes also referred to herein as a "XR environment" or a "virtual environment" or a "graphical environment" or a "3D environment") for a user 150 and optionally other users. In some implementations, the controller 110 includes a suitable combination of software, firmware, and/or hardware. The controller 110 is described in greater detail below with respect to FIG. 2. In some implementations, the controller 110 is a computing device that is local or remote relative to the physical environment 105. For example, the controller 110 is a local server located within the physical environment 105. In another example, the controller 110 is a remote server located outside of the physical environment 105 (e.g., a cloud server, central server, etc.). In some implementations, the controller 110 is communicatively coupled with the electronic device 120 via one or more wired or wireless communication channels 144 (e.g., BLU-ETOOTH, IEEE 802.11x, IEEE 802.16x, IEEE 802.3x, etc.). In some implementations, the functions of the controller 110 are provided by the electronic device 120. As such, in some implementations, the components of the controller 110 are integrated into the electronic device 120.

In some implementations, the electronic device 120 is configured to present audio and/or video (A/V) content to the user 150. In some implementations, the electronic device 120 is configured to present a user interface (UI) and/or an XR environment 128 to the user 150. In some implementations, the electronic device 120 includes a suitable combination of software, firmware, and/or hardware. The electronic device 120 is described in greater detail below with respect to FIG. 3.

According to some implementations, the electronic device 120 presents an XR experience to the user 150 while the user 150 is physically present within a physical environment 105 that includes a table 107 within the field-of-view (FOV) 111 of the electronic device 120. As such, in some implementations, the user 150 holds the electronic device 120 in his/her hand(s). In some implementations, while presenting the XR experience, the electronic device 120 is configured to present XR content (sometimes also referred to herein as "graphical content" or "virtual content"), including an XR cylinder 109, and to enable video pass-through of the physical environment 105 (e.g., including the table 107 or a representations thereof) on a display 122. For example, the XR environment 128, including the XR cylinder 109, is volumetric or three-dimensional (3D).

In one example, the XR cylinder 109 corresponds to head/display-locked content such that the XR cylinder 109 remains displayed at the same location on the display 122 as the FOV 111 changes due to translational and/or rotational movement of the electronic device 120. As another example, the XR cylinder 109 corresponds to world/object-locked content such that the XR cylinder 109 remains displayed at its origin location as the FOV 111 changes due to translational and/or rotational movement of the electronic device 120. As such, in this example, if the FOV 111 does not include the origin location, the displayed XR environment 128 will not include the XR cylinder 109. As another example, the XR cylinder 109 corresponds to body-locked content such that it remains at a positional and rotational offset from the body of the user 150. In some examples, the electronic device 120 corresponds to a near-eye system, mobile phone, tablet, laptop, wearable computing device, or the like.

In some implementations, the display 122 corresponds to an additive display that enables optical see-through of the physical environment 105 including the table 107. For example, the display 122 corresponds to a transparent lens, and the electronic device 120 corresponds to a pair of glasses worn by the user 150. As such, in some implementations, the electronic device 120 presents a user interface by projecting the XR content (e.g., the XR cylinder 109) onto the additive display, which is, in turn, overlaid on the physical environment 105 from the perspective of the user 150. In some implementations, the electronic device 120 presents the user interface by displaying the XR content (e.g., the XR cylinder 109) on the additive display, which is, in turn, overlaid on the physical environment 105 from the perspective of the user 150.

In some implementations, the user 150 wears the electronic device 120 such as a near-eye system. As such, the electronic device 120 includes one or more displays provided to display the XR content (e.g., a single display or one for each eye). For example, the electronic device 120 encloses the FOV of the user 150. In such implementations, the electronic device 120 presents the XR environment 128 by displaying data corresponding to the XR environment 128 on the one or more displays or by projecting data corresponding to the XR environment 128 onto the retinas of the user 150.

In some implementations, the electronic device 120 includes an integrated display (e.g., a built-in display) that displays the XR environment 128. In some implementations, the electronic device 120 includes a head-mountable enclosure. In various implementations, the head-mountable enclosure includes an attachment region to which another device with a display can be attached. For example, in some implementations, the electronic device 120 can be attached to the head-mountable enclosure. In various implementations, the head-mountable enclosure is shaped to form a receptacle for receiving another device that includes a display (e.g., the electronic device 120). For example, in some implementations, the electronic device 120 slides/snaps into or otherwise attaches to the head-mountable enclosure. In some implementations, the display of the device attached to the head-mountable enclosure presents (e.g., displays) the XR environment 128. In some implementations, the electronic device 120 is replaced with an XR chamber, enclosure, or room configured to present XR content in which the user 150 does not wear the electronic device 120.

In some implementations, the controller 110 and/or the electronic device 120 cause an XR representation of the user 150 to move within the XR environment 128 based on movement information (e.g., body pose data, eye tracking data, hand/limb/finger/extremity tracking data, etc.) from the electronic device 120 and/or optional remote input devices within the physical environment 105. In some implementations, the optional remote input devices correspond to fixed or movable sensory equipment within the physical environment 105 (e.g., image sensors, depth sensors, infrared (IR) sensors, event cameras, microphones, etc.). In some implementations, each of the remote input devices is configured to collect/capture input data and provide the input data to the controller 110 and/or the electronic device 120 while the user 150 is physically within the physical environment 105. In some implementations, the remote input devices include microphones, and the input data includes audio data associated with the user 150 (e.g., speech samples). In some implementations, the remote input devices include image sensors (e.g., cameras), and the input data includes images of the user 150. In some implementations, the input data characterizes body poses of the user 150 at different times. In some implementations, the input data characterizes head poses of the user 150 at different times. In some implementations, the input data characterizes hand tracking information associated with the hands of the user 150 at different times. In some implementations, the input data characterizes the velocity and/or acceleration of body parts of the user 150 such as his/her hands. In some implementations, the input data indicates joint positions and/or joint orientations of the user 150. In some implementations, the remote input devices include feedback devices such as speakers, lights, or the like.

FIG. 2 is a block diagram of an example of the controller 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some implementations, the one or more communication buses 204 include circuitry that interconnects and controls communications between system components. In some implementations, the one or more I/O devices 206 include at least one of a keyboard, a mouse, a touchpad, a touchscreen, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RAM), or other random-access solid-state memory devices. In some implementations, the memory 220 includes non-volatile memory, such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some implementations, the memory 220 or the non-transitory computer readable storage medium of the memory 220 stores the following programs, modules and data structures, or a subset thereof described below with respect to FIG. 2.

An operating system 230 includes procedures for handling various basic system services and for performing hardware dependent tasks.

In some implementations, a data obtainer 242 is configured to obtain data (e.g., captured image frames of the physical environment 105, presentation data, input data, user interaction data, camera pose tracking information, eye tracking information, head/body pose tracking information, hand/limb/finger/extremity tracking information, sensor data, location data, etc.) from at least one of the I/O devices 206 of the controller 110, the I/O devices and sensors 306 of the electronic device 120, and the optional remote input devices. To that end, in various implementations, the data obtainer 242 includes instructions and/or logic therefor, and heuristics and metadata therefor.

In some implementations, a mapper and locator engine 244 is configured to map the physical environment 105 and to track the position/location of at least the electronic device 120 or the user 150 with respect to the physical environment 105. To that end, in various implementations, the mapper and locator engine 244 includes instructions and/or logic therefor, and heuristics and metadata therefor.

In some implementations, a data transmitter 246 is configured to transmit data (e.g., presentation data such as rendered image frames associated with the XR environment, location data, etc.) to at least the electronic device 120 and optionally one or more other devices. To that end, in various implementations, the data transmitter 246 includes instructions and/or logic therefor, and heuristics and metadata therefor.

In some implementations, a privacy architecture 408 is configured to ingest data and filter user information and/or identifying information within the data based on one or more privacy filters. The privacy architecture 408 is described in more detail below with reference to FIG. 4A. To that end, in various implementations, the privacy architecture 408 includes instructions and/or logic therefor, and heuristics and metadata therefor.

Figure 4A:
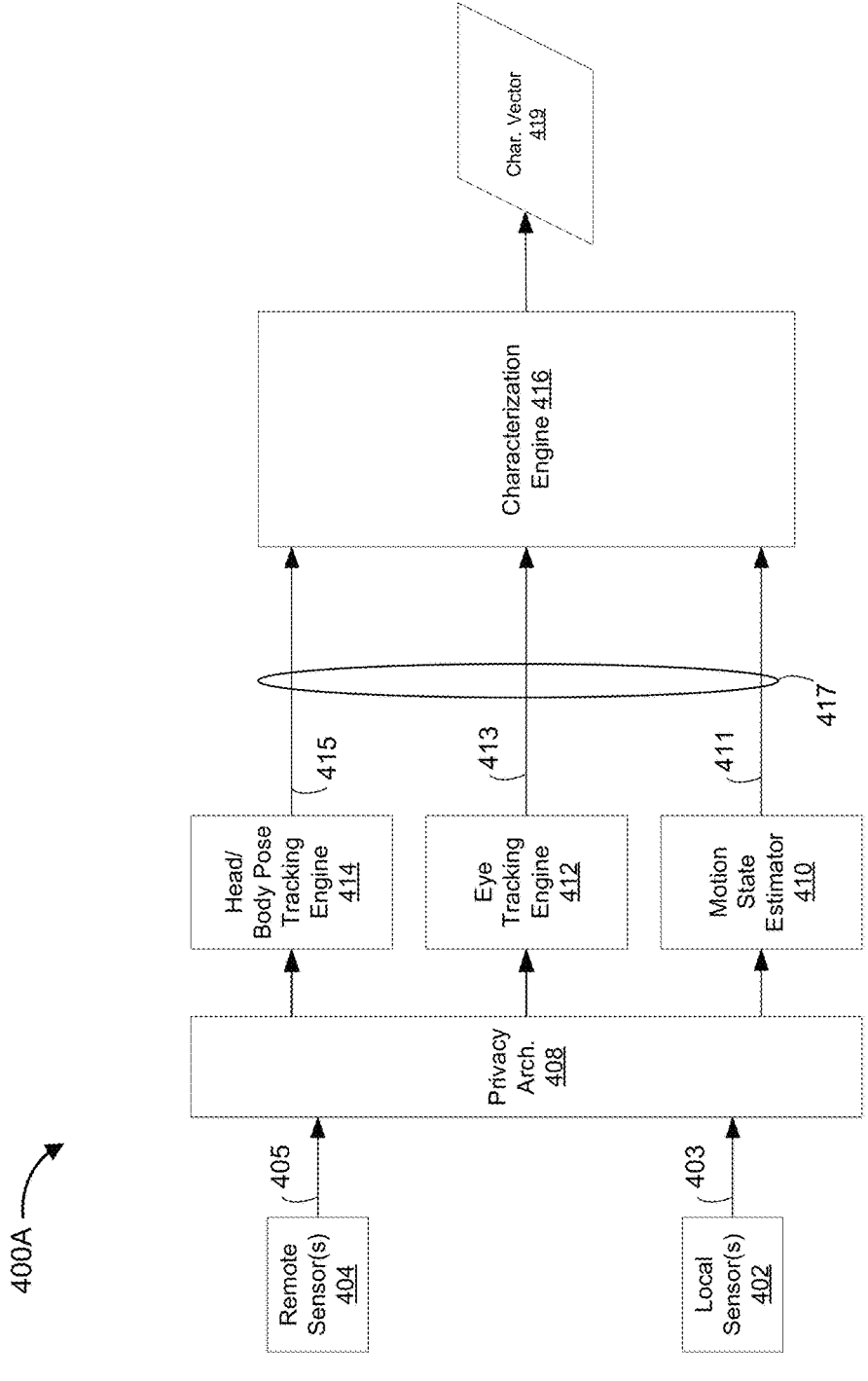
FIG. 4A is a block diagram of a first portion of a data processing architecture in accordance with some implementations.

In some implementations, a motion state estimator 410 is configured to obtain (e.g., receive, retrieve, or determine/generate) a motion state vector 411 associated with the electronic device 120 (and the user 150) (e.g., including a current motion state associated with the electronic device 120) based on input data and update the motion state vector 411 over time. For example, as shown in FIG. 4B, the motion state vector 411 includes a motion state descriptor 422 for the electronic device 120 (e.g., stationary, in-motion, walking, running, cycling, operating or riding in an automobile car, operating or riding in a boat, operating or riding in a bus, operating or riding in a train, operating or riding in an aircraft, or the like), translational movement values 424 associated with the electronic device 120 (e.g., a heading, a velocity value, an acceleration value, etc.), angular movement values 426 associated with the electronic device 120 (e.g., an angular velocity value, an angular acceleration value, and/or the like for each of the pitch, roll, and yaw dimensions), and/or the like. The motion state estimator 410 is described in more detail below with reference to FIG. 4A. To that end, in various implementations, the motion state estimator 410 includes instructions and/or logic therefor, and heuristics and metadata therefor.

In some implementations, an eye tracking engine 412 is configured to obtain (e.g., receive, retrieve, or determine/generate) an eye tracking vector 413 as shown in FIG. 4B (e.g., with a gaze direction) based on the input data and update the eye tracking vector 413 over time. For example, the gaze direction indicates a point (e.g., associated with x, y, and z coordinates relative to the physical environment 105 or the world-at-large), a physical object, or a region of interest (ROI) in the physical environment 105 at which the user 150 is currently looking. As another example, the gaze direction indicates a point (e.g., associated with x, y, and z coordinates relative to the XR environment 128), an XR object, or a ROI in the XR environment 128 at which the user 150 is currently looking. The eye tracking engine 412 is described in more detail below with reference to FIG. 4A. To that end, in various implementations, the eye tracking engine 412 includes instructions and/or logic therefor, and heuristics and metadata therefor.

In some implementations, a head/body pose tracking engine 414 is configured to obtain (e.g., receive, retrieve, or determine/generate) a pose characterization vector 415 based on the input data and update the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like. The head/body pose tracking engine 414 is described in more detail below with reference to FIG. 4A. To that end, in various implementations, the head/body pose tracking engine 414 includes instructions and/or logic therefor, and heuristics and metadata therefor. In some implementations, the motion state estimator 410, the eye tracking engine 412, and the head/body pose tracking engine 414 may be located on the electronic device 120 in addition to or in place of the controller 110.

In some implementations, a content selector 522 is configured to select XR content (sometimes also referred to herein as "graphical content" or "virtual content") from a content library 525 based on one or more user requests and/or inputs (e.g., a voice command, a selection from a user interface (UI) menu of XR content items or virtual agents (VAs), and/or the like). The content selector 522 is described in more detail below with reference to FIG. 4A. To that end, in various implementations, the content selector 522 includes instructions and/or logic therefor, and heuristics and metadata therefor.

In some implementations, a content library 525 includes a plurality of content items such as audio/visual (A/V) content, virtual agents (VAs), and/or XR content, objects, items, scenery, etc. As one example, the XR content includes 3D reconstructions of user captured videos, movies, TV episodes, and/or other XR content. In some implementations, the content library 525 is pre-populated or manually authored by the user 150. In some implementations, the content library 525 is located local relative to the controller 110. In some implementations, the content library 525 is located remote from the controller 110 (e.g., at a remote server, a cloud server, or the like).

In some implementations, a characterization engine 416 is configured to determine/generate a characterization vector 419 based on at least one of the motion state vector 411, the eye tracking vector 413, and the pose characterization vector 415 as shown in FIG. 4A. In some implementations, the characterization engine 416 is also configured to update the pose characterization vector 419 over time. As shown in FIG. 4B, the characterization vector 419 includes motion state information 452, gaze direction information 454, head pose information 456A, body pose information 456AB, extremity tracking information 456AC, location information 458, and/or the like. The characterization engine 416 is described in more detail below with reference to FIG. 4A. To that end, in various implementations, the characterization engine 416 includes instructions and/or logic therefor, and heuristics and metadata therefor.

Figure 4C:
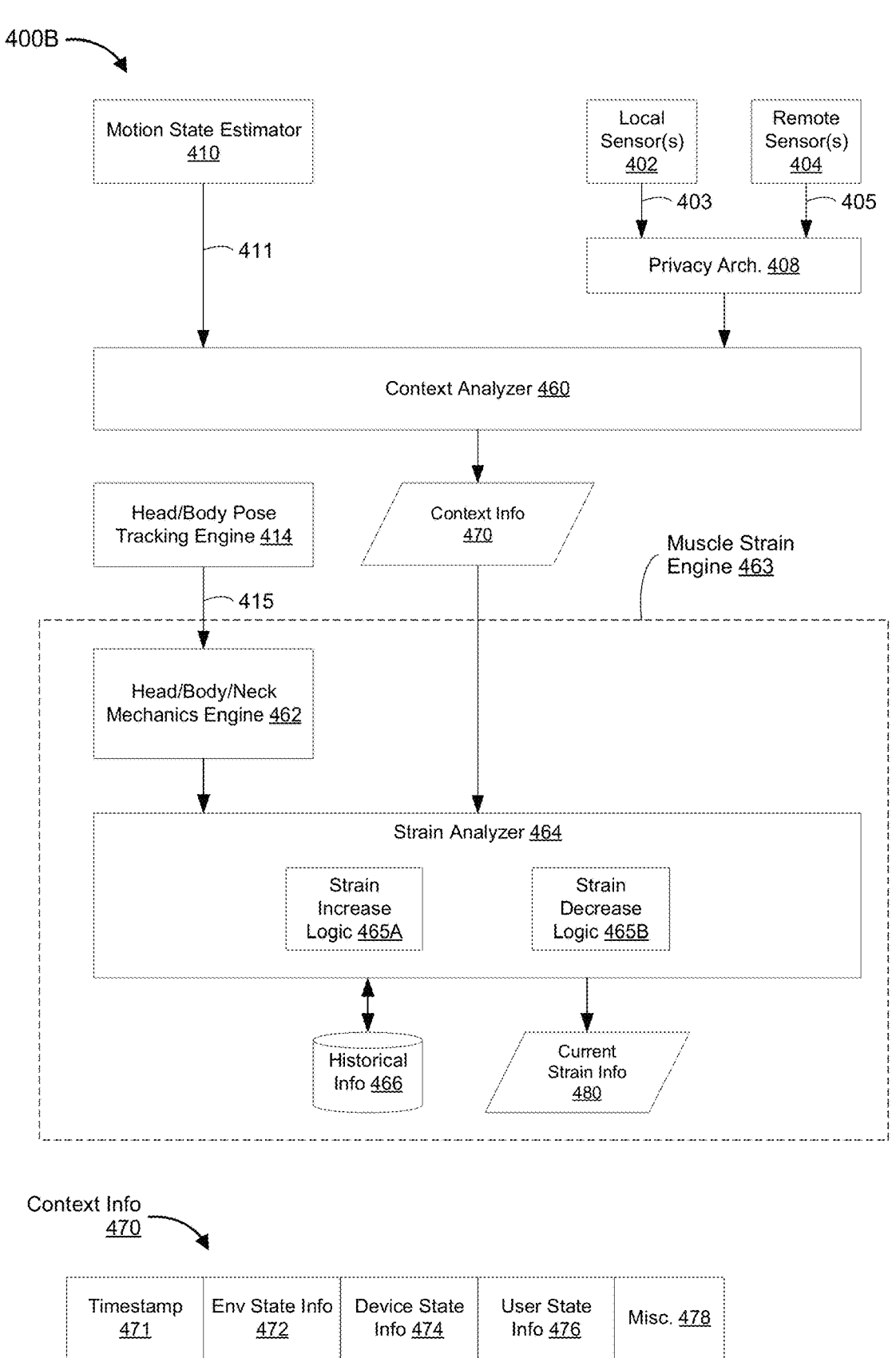
FIG. 4C is a block diagram of a second portion of a data processing architecture in accordance with some implementations.

In some implementations, a context analyzer 460 is configured to obtain (e.g., receive, retrieve, or determine/generate) a context information vector 470 based on input data shown in FIG. 4C and update the context information vector 470 over time. As shown in FIG. 4C, the context information vector 470 includes environmental state information 472, device state information 474, and user state information 476. The context analyzer 460 is described in more detail below with reference to FIG. 4C. To that end, in various implementations, the context analyzer 460 includes instructions and/or logic therefor, and heuristics and metadata therefor.

Figure 4D:
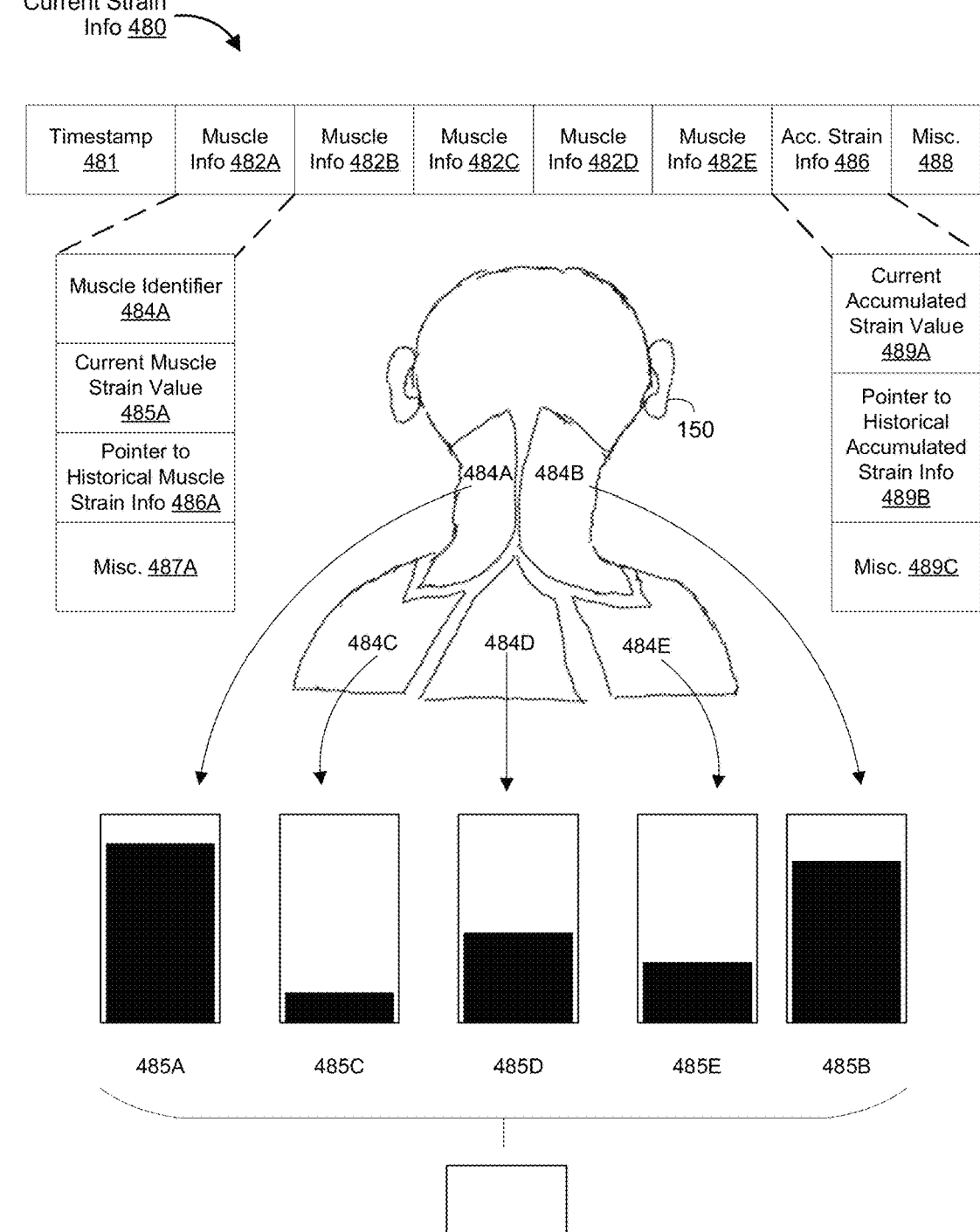
FIG. 4D illustrates example data structures in accordance with some implementations.

In some implementations, a muscle strain engine 463 is configured to obtain (e.g., receive, retrieve, or determine/generate) current strain information 480 based on input data shown in FIG. 4C and update the current strain information 480 over time. As shown in FIG. 4D, the current strain information 480 includes: muscle information 482A associated with a first muscle or muscle group/region; muscle information 482B associated with a second muscle or muscle group/region; muscle information 482C associated with a third muscle or muscle group/region; muscle information 482D associated with a fourth muscle or muscle group/region; muscle information 482E associated with a fifth muscle or muscle group/region; and current accumulated strain information 486. To that end, in various implementations, the muscle strain engine 463 includes a head/body/neck mechanics engine 462 and a strain analyzer 464 with strain increase logic 465A and strain decrease logic 465B. The muscle strain engine 463 is described in more detail below with reference to FIG. 4C. To that end, in various implementations, the muscle strain engine 463 includes instructions and/or logic therefor, and heuristics and metadata therefor.

In some implementations, a posture awareness engine 468A is configured to determine/generate tiered posture awareness feedback 469. The posture awareness engine 468A is described in more detail below with reference to FIG. 4E. To that end, in various implementations, the posture awareness engine 468A includes instructions and/or logic therefor, and heuristics and metadata therefor.

In some implementations, an application programing interface (API) 468B is configured to provide access to the current strain information 480 to at least one of: the operating system of the controller 110, the electronic device 120, or a combination thereof; third-party programs or applications; and/or the like. As such, the current strain information 480 may be used in various downstream processes. The API 468B is described in more detail below with reference to FIG. 4E. To that end, in various implementations, the API 468B includes instructions and/or logic therefor, and heuristics and metadata therefor.

In some implementations, a content manager 530 is configured to manage and update the layout, setup, structure, and/or the like for the XR environment 128 including one or more of VA(s), XR content, one or more user interface (UI) elements associated with the XR content, and/or the like.

The content manager 530 is described in more detail below with reference to FIG. 5. To that end, in various implementations, the content manager 530 includes instructions and/or logic therefor, and heuristics and metadata therefor. In some implementations, the content manager 530 includes a frame buffer 532, a content updater 534, and a feedback engine 536. In some implementations, the frame buffer 532 includes XR content, a rendered image frame, and/or the like for one or more past instances and/or frames.

In some implementations, the content updater 534 is configured to modify the XR environment 128 over time based on translational or rotational movement of the electronic device 120 or physical objects within the physical environment 105, user inputs (e.g., a change in context, hand/extremity tracking inputs, eye tracking inputs, touch inputs, voice commands, modification/manipulation inputs with the physical object, and/or the like), and/or the like. To that end, in various implementations, the content updater 534 includes instructions and/or logic therefor, and heuristics and metadata therefor.

In some implementations, the feedback engine 536 is configured to generate sensory feedback (e.g., visual feedback such as text or lighting changes, audio feedback, haptic feedback, etc.) associated with the XR environment 128. To that end, in various implementations, the feedback engine 536 includes instructions and/or logic therefor, and heuristics and metadata therefor.

In some implementations, a rendering engine 550 is configured to render an XR environment 128 (sometimes also referred to herein as a "graphical environment" or "virtual environment") or image frame associated therewith as well as the VA(s), XR content, one or more UI elements associated with the XR content, and/or the like. To that end, in various implementations, the rendering engine 550 includes instructions and/or logic therefor, and heuristics and metadata therefor. In some implementations, the rendering engine 550 includes a pose determiner 552, a renderer 554, an optional image processing architecture 556, and an optional compositor 558. One of ordinary skill in the art will appreciate that the optional image processing architecture 556 and the optional compositor 558 may be present for video pass-through configurations but may be removed for fully VR or optical see-through configurations.

In some implementations, the pose determiner 552 is configured to determine a current camera pose of the electronic device 120 and/or the user 150 relative to the A/V content and/or XR content. The pose determiner 552 is described in more detail below with reference to FIG. 5. To that end, in various implementations, the pose determiner 552 includes instructions and/or logic therefor, and heuristics and metadata therefor.

In some implementations, the renderer 554 is configured to render the A/V content and/or the XR content according to the current camera pose relative thereto. The renderer 554 is described in more detail below with reference to FIG. 5. To that end, in various implementations, the renderer 554 includes instructions and/or logic therefor, and heuristics and metadata therefor.

In some implementations, the image processing architecture 556 is configured to obtain (e.g., receive, retrieve, or capture) an image stream including one or more images of the physical environment 105 from the current camera pose of the electronic device 120 and/or the user 150. In some implementations, the image processing architecture 556 is also configured to perform one or more image processing operations on the image stream such as warping, color correction, gamma correction, sharpening, noise reduction, white balance, and/or the like. The image processing architecture 556 is described in more detail below with reference to FIG. 5. To that end, in various implementations, the image processing architecture 556 includes instructions and/or logic therefor, and heuristics and metadata therefor.

In some implementations, the compositor 558 is configured to composite the rendered A/V content and/or XR content with the processed image stream of the physical environment 105 from the image processing architecture 556 to produce rendered image frames of the XR environment 128 for display. The compositor 558 is described in more detail below with reference to FIG. 5. To that end, in various implementations, the compositor 558 includes instructions and/or logic therefor, and heuristics and metadata therefor.

Although the data obtainer 242, the mapper and locator engine 244, the data transmitter 246, the privacy architecture 408, the motion state estimator 410, the eye tracking engine 412, the head/body pose tracking engine 414, the characterization engine 416, the context analyzer 460, the muscle strain engine 463, the posture awareness engine 468A, the API 468B, the content selector 522, the content manager 530, and the rendering engine 550 are shown as residing on a single device (e.g., the controller 110), it should be understood that in other implementations, any combination of the data obtainer 242, the mapper and locator engine 244, the data transmitter 246, the privacy architecture 408, the motion state estimator 410, the eye tracking engine 412, the head/body pose tracking engine 414, the characterization engine 416, the context analyzer 460, the muscle strain engine 463, the posture awareness engine 468A, the API 468B, the content selector 522, the content manager 530, and the rendering engine 550 may be located in separate computing devices.

In some implementations, the functions and/or components of the controller 110 are combined with or provided by the electronic device 120 shown below in FIG. 3. Moreover, FIG. 2 is intended more as a functional description of the various features which may be present in a particular implementation as opposed to a structural schematic of the implementations described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

Figure 3:
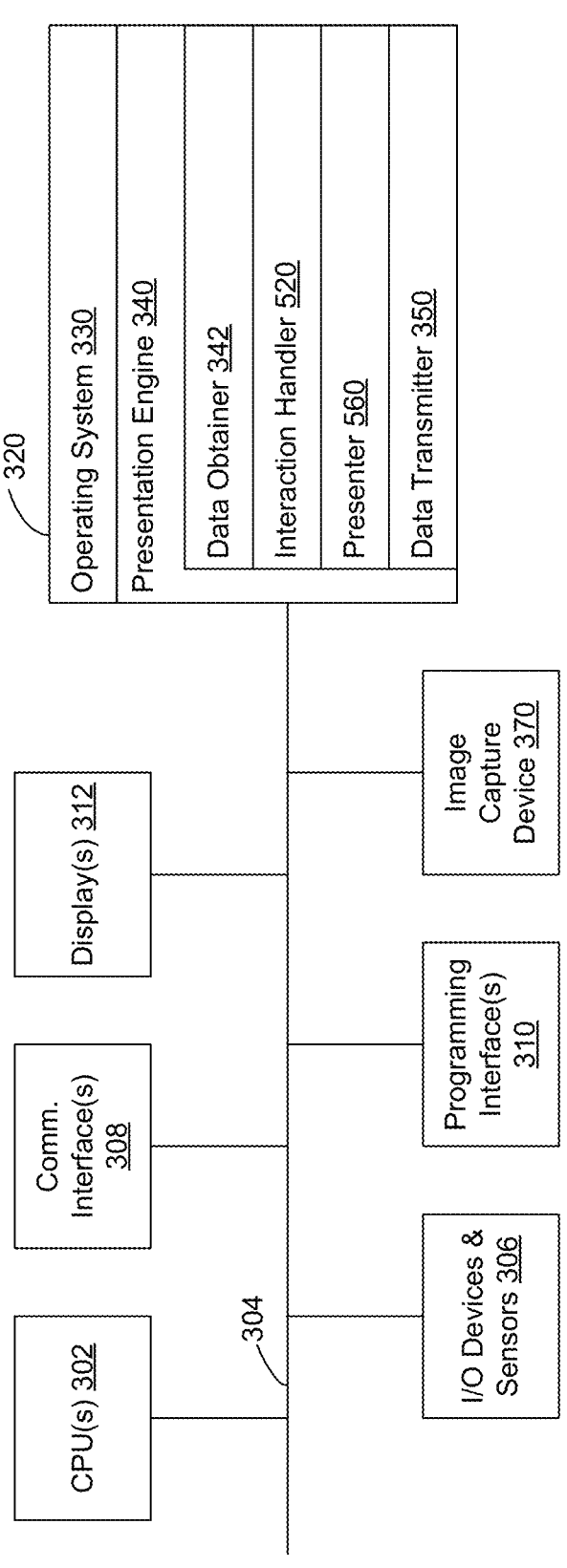
FIG. 3 is a block diagram of an example electronic device in accordance with some implementations.

FIG. 3 is a block diagram of an example of the electronic device 120 (e.g., a mobile phone, tablet, laptop, near-eye system, wearable computing device, or the like) in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the electronic device 120 includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 310, one or more displays 312, an image capture device 370 (e.g., one or more optional interior-facing and/or exterior-facing image sensors), a memory 320, and one or more communication buses 304 for interconnecting these and various other components.

In some implementations, the one or more communication buses 304 include circuitry that interconnects and controls communications between system components. In some implementations, the one or more I/O devices and sensors 306 include at least one of an inertial measurement unit (IMU), an accelerometer, a gyroscope, a magnetometer, a thermometer, one or more physiological sensors (e.g., blood pressure monitor, heart rate monitor, blood oximetry monitor, blood glucose monitor, etc.), one or more microphones, one or more speakers, a haptics engine, a heating and/or cooling unit, a skin shear engine, one or more depth sensors (e.g., structured light, time-of-flight, LiDAR, or the like), a localization and mapping engine, an eye tracking engine, a head/body pose tracking engine, a hand/limb/finger/extremity tracking engine, a camera pose tracking engine, and/or the like.

In some implementations, the one or more displays 312 are configured to present the XR environment to the user. In some implementations, the one or more displays 312 are also configured to present flat video content to the user (e.g., a 2-dimensional or "flat" AVI, FLV, WMV, MOV, MP4, or the like file associated with a TV episode or a movie, or live video pass-through of the physical environment 105). In some implementations, the one or more displays 312 correspond to touchscreen displays (e.g., similar to the display 122 in FIG. 1). In some implementations, the one or more displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more displays 312 correspond to diffractive, reflective, polarized, holographic, etc. waveguide displays. For example, the electronic device 120 includes a single display such as the display 122. In another example, the electronic device 120 includes a display for each eye of the user. In some implementations, the one or more displays 312 are capable of presenting AR and VR content. In some implementations, the one or more displays 312 are capable of presenting AR or VR content.

In some implementations, the image capture device 370 correspond to one or more RGB cameras (e.g., with a complementary metal-oxide-semiconductor (CMOS) image sensor or a charge-coupled device (CCD) image sensor), IR image sensors, event-based cameras, and/or the like. In some implementations, the image capture device 370 includes a lens assembly, a photodiode, and a front-end architecture. In some implementations, the image capture device 370 includes exterior-facing and/or interior-facing image sensors.

The memory 320 includes high-speed random-access memory, such as DRAM, SRAM, DDR RAM, or other random-access solid-state memory devices. In some implementations, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some implementations, the memory 320 or the non-transitory computer readable storage medium of the memory 320 stores the following programs, modules and data structures, or a subset thereof including an optional operating system 330 and a presentation engine 340.

The operating system 330 includes procedures for handling various basic system services and for performing hardware dependent tasks. In some implementations, the presentation engine 340 is configured to present media items and/or XR content to the user via the one or more displays 312. To that end, in various implementations, the presentation engine 340 includes a data obtainer 342, an interaction handler 520, a presenter 560, and a data transmitter 350.

In some implementations, the data obtainer 342 is configured to obtain data (e.g., presentation data such as rendered image frames associated with the user interface or the XR environment, input data, user interaction data, head tracking information, camera pose tracking information, eye tracking information, hand/limb/finger/extremity tracking information, sensor data, location data, etc.) from at least one of the I/O devices and sensors 306 of the electronic device 120, the controller 110, and the remote input devices. To that end, in various implementations, the data obtainer 342 includes instructions and/or logic therefor, and heuristics and metadata therefor.

In some implementations, the interaction handler 520 is configured to detect user interactions (e.g., gestural inputs detected via hand/extremity tracking, eye gaze inputs detected via eye tracking, voice commands, etc.) with the presented A/V content and/or XR content. To that end, in various implementations, the interaction handler 520 includes instructions and/or logic therefor, and heuristics and metadata therefor.

In some implementations, the presenter 560 is configured to present and update A/V content and/or XR content (e.g., the rendered image frames associated with the user interface or the XR environment 128 including the VA(s), the XR content, one or more UI elements associated with the XR content, and/or the like) via the one or more displays 312. To that end, in various implementations, the presenter 560 includes instructions and/or logic therefor, and heuristics and metadata therefor.

In some implementations, the data transmitter 350 is configured to transmit data (e.g., presentation data, location data, user interaction data, head tracking information, camera pose tracking information, eye tracking information, hand/limb/finger/extremity tracking information, etc.) to at least the controller 110. To that end, in various implementations, the data transmitter 350 includes instructions and/or logic therefor, and heuristics and metadata therefor.

Although the data obtainer 342, the interaction handler 520, the presenter 560, and the data transmitter 350 are shown as residing on a single device (e.g., the electronic device 120), it should be understood that in other implementations, any combination of the data obtainer 342, the interaction handler 520, the presenter 560, and the data transmitter 350 may be located in separate computing devices.

Moreover, FIG. 3 is intended more as a functional description of the various features which may be present in a particular implementation as opposed to a structural schematic of the implementations described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various implementations. The actual number of modules and the division of particular functions and how features are allocated among them will vary from one implementation to another and, in some implementations, depends in part on the particular combination of hardware, software, and/or firmware chosen for a particular implementation.

FIG. 4A is a block diagram of a first portion 400A of an example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the first portion 400A of the data processing architecture is included in a computing system such as the controller 110 shown in FIGS. 1 and 2; the electronic device 120 shown in FIGS. 1 and 3; and/or a suitable combination thereof.

As shown in FIG. 4A, one or more local sensors 402 of the controller 110, the electronic device 120, and/or a combination thereof obtain local sensor data 403 associated with the physical environment 105. For example, the local sensor data 403 includes images or a stream thereof of the physical environment 105, simultaneous location and mapping (SLAM) information for the physical environment 105 and the location of the electronic device 120 or the user 150 relative to the physical environment 105, ambient lighting information for the physical environment 105, ambient audio information for the physical environment 105, acoustic information for the physical environment 105, dimensional information for the physical environment 105, semantic labels for objects within the physical environment 105, and/or the like. In some implementations, the local sensor data 403 includes un-processed or post-processed information.

Similarly, as shown in FIG. 4A, one or more remote sensors 404 associated with the optional remote input devices within the physical environment 105 obtain remote sensor data 405 associated with the physical environment 105. For example, the remote sensor data 405 includes images or a stream thereof of the physical environment 105, SLAM information for the physical environment 105 and the location of the electronic device 120 or the user 150 relative to the physical environment 105, ambient lighting information for the physical environment 105, ambient audio information for the physical environment 105, acoustic information for the physical environment 105, dimensional information for the physical environment 105, semantic labels for objects within the physical environment 105, and/or the like. In some implementations, the remote sensor data 405 includes un-processed or post-processed information.

According to some implementations, the privacy architecture 408 ingests the local sensor data 403 and the remote sensor data 405. In some implementations, the privacy architecture 408 includes one or more privacy filters associated with user information and/or identifying information. In some implementations, the privacy architecture 408 includes an opt-in feature where the electronic device 120 informs the user 150 as to what user information and/or identifying information is being monitored and how the user information and/or the identifying information will be used.

In some implementations, the privacy architecture 408 selectively prevents and/or limits the data processing architecture 400A/400B/400C or portions thereof from obtaining and/or transmitting the user information. To this end, the privacy architecture 408 receives user preferences and/or selections from the user 150 in response to prompting the user 150 for the same. In some implementations, the privacy architecture 408 prevents the data processing architecture 400A/400B/400C from obtaining and/or transmitting the user information unless and until the privacy architecture 408 obtains informed consent from the user 150. In some implementations, the privacy architecture 408 anonymizes (e.g., scrambles, obscures, encrypts, and/or the like) certain types of user information. For example, the privacy architecture 408 receives user inputs designating which types of user information the privacy architecture 408 anonymizes. As another example, the privacy architecture 408 anonymizes certain types of user information likely to include sensitive and/or identifying information, independent of user designation (e.g., automatically).

According to some implementations, the motion state estimator 410 obtains the local sensor data 403 and the remote sensor data 405 after it has been subjected to the privacy architecture 408. In some implementations, the motion state estimator 410 obtains (e.g., receives, retrieves, or determines/generates) a motion state vector 411 based on the input data and updates the motion state vector 411 over time.

FIG. 4B shows an example data structure for the motion state vector 411 in accordance with some implementations. As shown in FIG. 4B, the motion state vector 411 may correspond to an N-tuple characterization vector or characterization tensor that includes a timestamp 421 (e.g., the most recent time the motion state vector 411 was updated), a motion state descriptor 422 for the electronic device 120 (e.g., stationary, in-motion, running, walking, cycling, driving or riding in a car, driving or riding in a boat, driving or riding in a bus, riding in a train, riding in a plane, or the like), translational movement values 424 associated with the electronic device 120 (e.g., a heading, a displacement value, a velocity value, an acceleration value, a jerk value, etc.), angular movement values 426 associated with the electronic device 120 (e.g., an angular displacement value, an angular velocity value, an angular acceleration value, an angular jerk value, and/or the like for each of the pitch, roll, and yaw dimensions), and/or miscellaneous information 428. One of ordinary skill in the art will appreciate that the data structure for the motion state vector 411 in FIG. 4B is merely an example that may include different information portions in various other implementations and be structured in myriad ways in various other implementations.

According to some implementations, the eye tracking engine 412 obtains the local sensor data 403 and the remote sensor data 405 after it has been subjected to the privacy architecture 408. In some implementations, the eye tracking engine 412 obtains (e.g., receives, retrieves, or determines/generates) an eye tracking vector 413 based on the input data and updates the eye tracking vector 413 over time.

FIG. 4B shows an example data structure for the eye tracking vector 413 in accordance with some implementations. As shown in FIG. 4B, the eye tracking vector 413 may correspond to an N-tuple characterization vector or characterization tensor that includes a timestamp 431 (e.g., the most recent time the eye tracking vector 413 was updated), one or more angular values 432 for a current gaze direction (e.g., roll, pitch, and yaw values), one or more translational values 434 for the current gaze direction (e.g., x, y, and z values relative to the physical environment 105, the world-at-large, and/or the like), and/or miscellaneous information 436. One of ordinary skill in the art will appreciate that the data structure for the eye tracking vector 413 in FIG. 4B is merely an example that may include different information portions in various other implementations and be structured in myriad ways in various other implementations.

For example, the gaze direction indicates a point (e.g., associated with x, y, and z coordinates relative to the physical environment 105 or the world-at-large), a physical object, or a region of interest (ROI) in the physical environment 105 at which the user 150 is currently looking. As another example, the gaze direction indicates a point (e.g., associated with x, y, and z coordinates relative to the XR environment 128), an XR object, or a region of interest (ROI) in the XR environment 128 at which the user 150 is currently looking.

According to some implementations, the head/body pose tracking engine 414 obtains the local sensor data 403 and the remote sensor data 405 after it has been subjected to the privacy architecture 408. In some implementations, the head/body pose tracking engine 414 obtains (e.g., receives, retrieves, or determines/generates) a pose characterization vector 415 based on the input data and updates the pose characterization vector 415 over time.

FIG. 4B shows an example data structure for the pose characterization vector 415 in accordance with some implementations. As shown in FIG. 4B, the pose characterization vector 415 may correspond to an N-tuple characterization vector or characterization tensor that includes a timestamp 441 (e.g., the most recent time the pose characterization vector 415 was updated), a head pose descriptor 442A (e.g., upward, downward, neutral, etc.), translational values for the head pose 442B, rotational values for the head pose 442C, a body pose descriptor 444A (e.g., standing, sitting, prone, etc.), translational values for body sections/extremities/limbs/joints 444B, rotational values for the body sections/extremities/limbs/joints 444C, and/or miscellaneous information 446. In some implementations, the pose characterization vector 415 also includes information associated with finger/hand/extremity tracking. One of ordinary skill in the art will appreciate that the data structure for the pose characterization vector 415 in FIG. 4B is merely an example that may include different information portions in various other implementations and be structured in myriad ways in various other implementations. According to some implementations, the motion state vector 411, the eye tracking vector 413 and the pose characterization vector 415 are collectively referred to as an input vector 417.

According to some implementations, the characterization engine 416 obtains the motion state vector 411, the eye tracking vector 413 and the pose characterization vector 415. In some implementations, the characterization engine 416 obtains (e.g., receives, retrieves, or determines/generates) the characterization vector 419 based on the motion state vector 411, the eye tracking vector 413, and the pose characterization vector 415.

FIG. 4B shows an example data structure for the characterization vector 419 in accordance with some implementations. As shown in FIG. 4B, the characterization vector 419 may correspond to an N-tuple characterization vector or characterization tensor that includes a timestamp 451 (e.g., the most recent time the characterization vector 419 was updated), motion state information 452 (e.g., the motion state descriptor 422), gaze direction information 454 (e.g., a function of the one or more angular values 432 and the one or more translational values 434 within the eye tracking vector 413), head pose information 456A (e.g., a function of the head pose descriptor 442A within the pose characterization vector 415), body pose information 456B (e.g., a function of the body pose descriptor 444A within the pose characterization vector 415), extremity tracking information 456C (e.g., a function of the body pose descriptor 444A within the pose characterization vector 415 that is associated with extremities of the user 150 that are being tracked by the controller 110, the electronic device 120, and/or a combination thereof), location information 458 (e.g., a household location such as a kitchen or living room, a vehicular location such as an automobile, plane, etc., and/or the like), and/or miscellaneous information 459.

FIG. 4C is a block diagram of a second portion 400B of the example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the second portion 400B of the data processing architecture is included in a computing system such as the controller 110 shown in FIGS. 1 and 2; the electronic device 120 shown in FIGS. 1 and 3; and/or a suitable combination thereof. FIG. 4C is similar to and adapted from FIG. 4A. Therefore, similar reference numbers are used in FIGS. 4A and 4C. As such, only the differences between FIGS. 4A and 4C will be described below for the sake of brevity.

According to some implementations, the context analyzer 460 obtains the motion state vector 411 from the motion state estimator 410. As shown in FIG. 4C, the context analyzer 460 also obtains the local sensor data 403 and the remote sensor data 405 after being subjected to the privacy architecture 408.

In some implementations, the context analyzer 460 obtains (e.g., receives, retrieves, or determines/generates) a context information vector 470 based on the input data and updates the context information vector 470 over time. FIG. 4C shows an example data structure for the context information vector 470 in accordance with some implementations. As shown in FIG. 4C, the context information vector 470 may correspond to an N-tuple characterization vector or characterization tensor that includes: a timestamp 471 (e.g., the most recent time the context information vector 470 was updated); environmental state information 472 associated with a current state of the physical environment 105 (e.g., ambient temperature information, ambient humidity information, ambient lighting information, ambient audio information, semantic labels for physical objects within the physical environment 105, locations for physical objects within the physical environment 105, etc.); device state information 474 associated with a current state of the controller 110, the electronic device 120, or a combination thereof, or the like (e.g., current foreground applications, current background applications, power/charge remaining, device temperature metrics, resource consumption metrics (e.g., CPU, RAM, storage, network I/O, etc.), etc.); user state information 476 associated with a current state of the user 150 (e.g., the characterization vector 419, physiological information associated with the user 150, the motion state descriptor 42, etc.); and miscellaneous information 478. One of ordinary skill in the art will appreciate that the data structure for the context information vector 470 in FIG. 4C is merely an example that may include different information portions in various other implementations and be structured in myriad ways in various other implementations.

According to some implementations, the head/body/neck mechanics engine 462 obtains (e.g., receives, retrieves, or determines/generates) displacement, velocity, acceleration, jerk, torque, etc. values for the head/body/neck of the user 150 based on changes to the pose characterization vector 415. In some implementations, the strain analyzer 464 determines current strain information 480 for one or more muscles or muscle groups based on: the displacement, velocity, acceleration, jerk, torque, etc. values for the head/body/neck of the user 150 from the head/body/neck mechanics engine 462; historical information 466; and the context information vector 470. In some implementations, the strain analyzer 464 determines the current strain information 480 based on strain increase logic 465A and/or strain decrease logic 465B. In some implementations, the historical information 466 corresponds to a local or remote storage repository, including: strain information for one or more previous time periods on an overall basis, individual muscle or muscle group/region basis, etc.; context information for one or more previous time periods; and/or displacement, velocity, acceleration, jerk, torque, etc. values for the head/body/neck of the user 150 for one or more previous time periods.

FIG. 4D shows an example data structure for the current strain information 480 in accordance with some implementations. As shown in FIG. 4C, the current strain information 480 may correspond to an N-tuple characterization vector or characterization tensor that includes: a timestamp 481; muscle information 482A associated with a first muscle or muscle group/region; muscle information 482B associated with a second muscle or muscle group/region; muscle information 482C associated with a third muscle or muscle group/region; muscle information 482D associated with a fourth muscle or muscle group/region; muscle information 482E associated with a fifth muscle or muscle group/region; accumulated strain information 486 associated with a function of the muscle information 482A-482E; and miscellaneous information 488. One of ordinary skill in the art will appreciate that the data structure for current strain information 480 in FIG. 4D is merely an example that may include different information portions in various other implementations and be structured in myriad ways in various other implementations.

As shown in FIG. 4D, the muscle information 482A for the first muscle or muscle group/region includes: a muscle identifier 484A for the first muscle or muscle group/region (e.g., a unique identifier, a label, a name, or the like for the first muscle or muscle group/region); a current muscle strain value 485A for the first muscle or muscle group/region; a pointer to historical muscle strain information 486A for the first muscle or muscle group/region within the historical information 466; and miscellaneous information 487A associated with the first muscle or muscle group/region.

As shown in FIG. 4D, for example, the muscle strain engine 463 determines current muscle strain values 485A, 485B, 485C, 485D, and 485E for muscles or muscle groups/regions 484A, 484B, 484C, 484D, and 484E, respectively, of the user 150. Furthermore, the muscle strain engine 463 updates (increases or decreases) the muscle strain values 485A, 485B, 485C, 485D, and 485E over time based on rotational and/or translational movement of the user 150 that triggers the strain increase logic 465A and/or the strain decrease logic 465B.

As shown in FIG. 4D, the accumulated strain information 486: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information 486. As shown in FIG. 4D, for example, the muscle strain engine 463 also determines a current accumulated strain value 489A and updates (increases or decreases) the current accumulated strain value 489A over time based on rotational and/or translational movement of the user 150 that triggers the strain increase logic 465A and/or the strain decrease logic 465B. As such, according to some implementations, the muscle strain engine 463 tracks strain values on an individual muscle or muscle group/region basis (e.g., the muscle information 482A-482E) as well as an overall strain value (e.g., the current accumulated strain information 486).

Figure 4E:
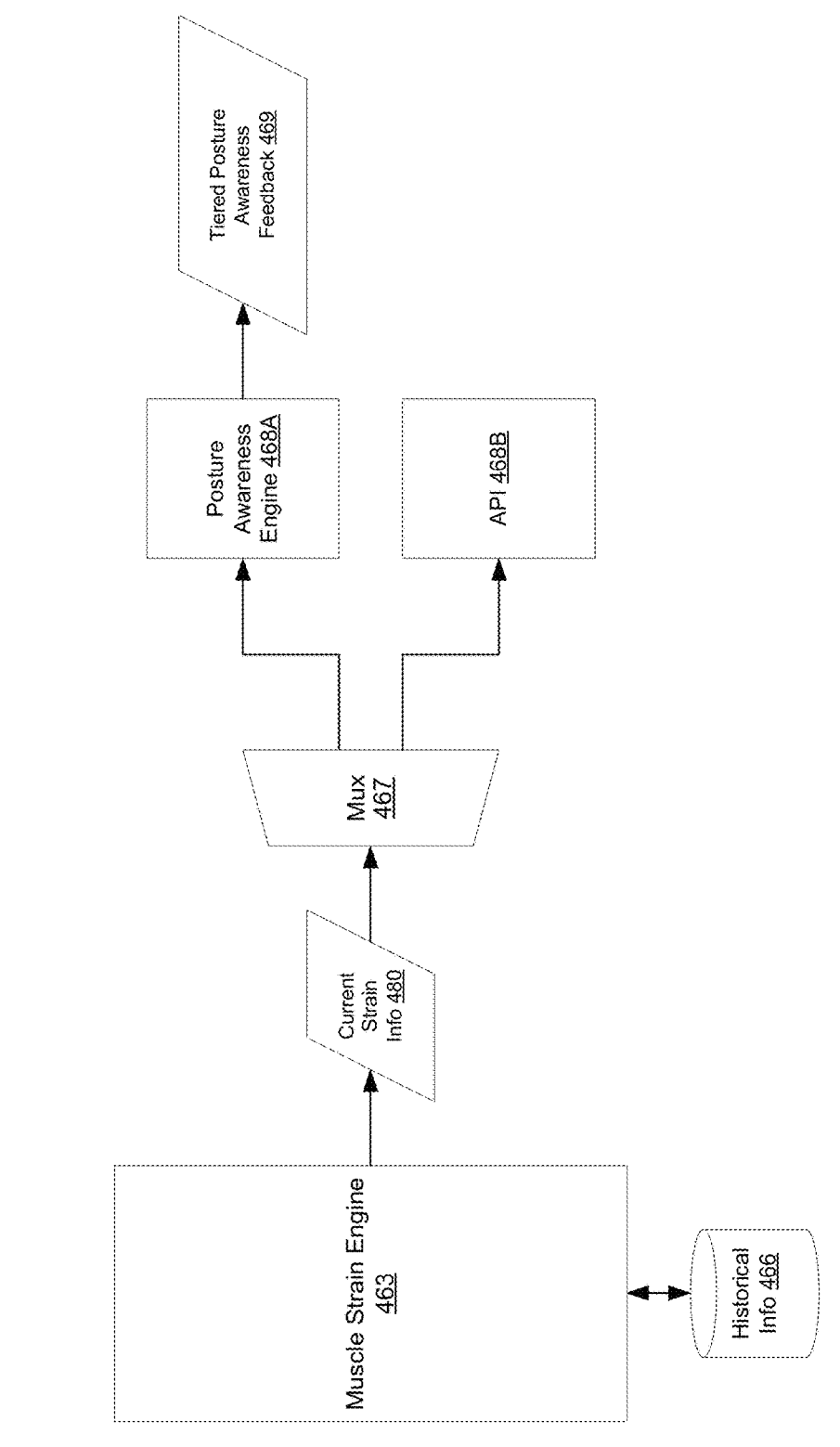
FIG. 4E is a block diagram of a third portion of a data processing architecture in accordance with some implementations.

FIG. 4E is a block diagram of a third portion 400C of the example data processing architecture in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the third portion 400C of the example data processing architecture is included in a computing system such as the controller 110 shown in FIGS. 1 and 2; the electronic device 120 shown in FIGS. 1 and 3; and/or a suitable combination thereof. FIG. 4E is similar to and adapted from FIGS. 4A and 4C. Therefore, similar reference numbers are used in FIGS. 4A and 4C. As such, only the differences between FIGS. 4A, 4C, and 4E will be described below for the sake of brevity.

As described above with respect to FIG. 4C, the muscle strain engine 463 determines a current strain information 480. As illustrated in FIG. 4E, the current strain information 480 is provided to a multiplexer (Mux) 467. In turn, the current strain information 480 is provided to at least one of a posture awareness engine 468A and an application programming interface (API) 468B. According to some implementations, the posture awareness engine 468A determines/generates tiered posture awareness feedback 469. The tiered posture awareness feedback 469 is described in greater detail below with reference to FIGS. 6A-6J. According to some implementations, the API 468B provides access to the current strain information 480 to at least one of: the operating system of the controller 110, the electronic device 120, or a combination thereof; third-party programs or applications; and/or the like. As such, the current strain information 480 may be used in various downstream processes.

Figure 5:
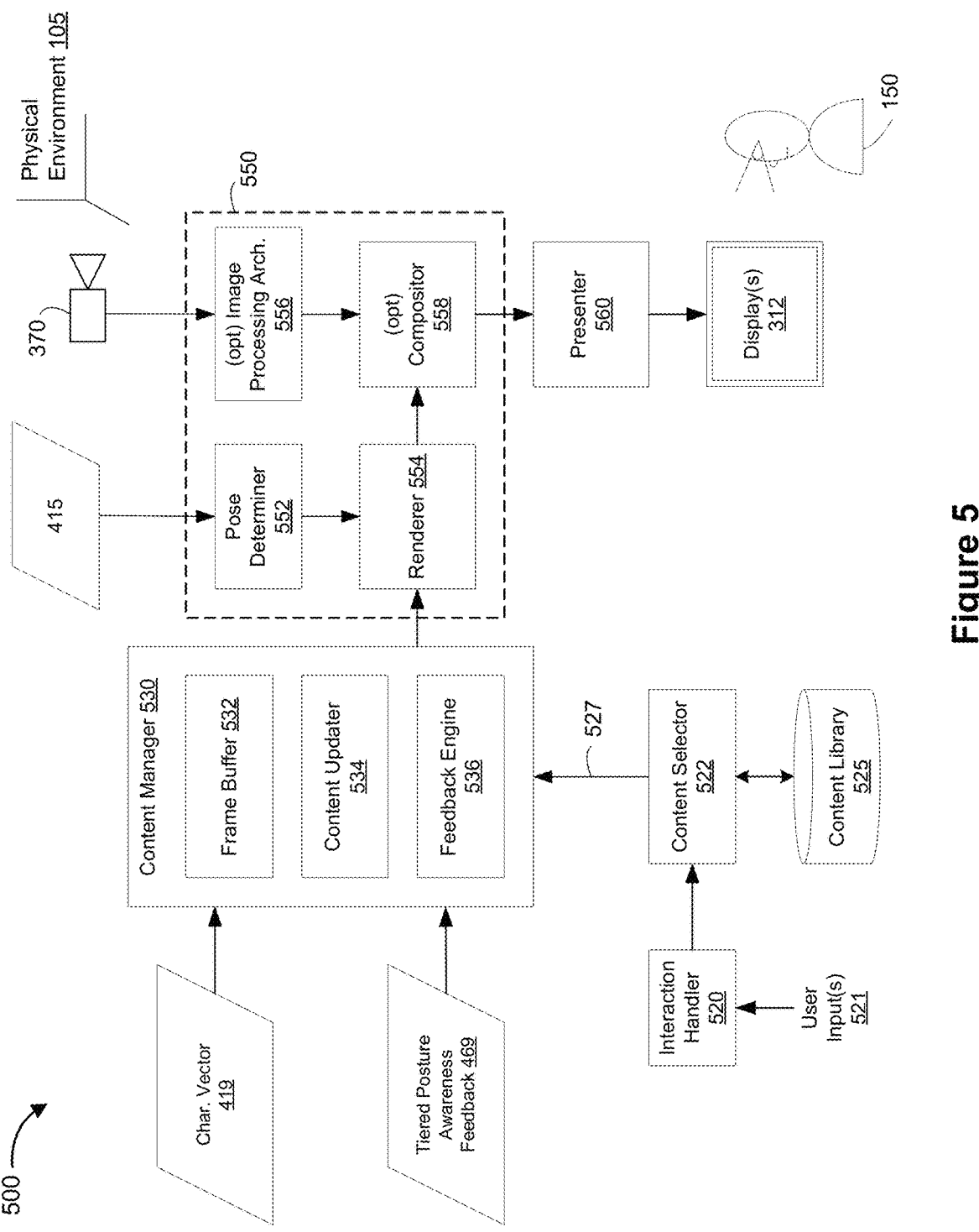
FIG. 5 is a block diagram of an example content delivery architecture in accordance with some implementations.

FIG. 5 is a block diagram of an example content delivery architecture 500 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the content delivery architecture is included in a computing system such as the controller 110 shown in FIGS. 1 and 2; the electronic device 120 shown in FIGS. 1 and 3; and/or a suitable combination thereof.

According to some implementations, the interaction handler 520 obtains (e.g., receives, retrieves, or detects) one or more user inputs 521 provided by the user 150 that are associated with selecting A/V content, one or more VAs, and/or XR content for presentation. For example, the one or more user inputs 521 correspond to a gestural input selecting XR content from a UI menu detected via hand/extremity tracking, an eye gaze input selecting XR content from the UI menu detected via eye tracking, a voice command selecting XR content from the UI menu detected via a microphone, and/or the like. In some implementations, the content selector 522 selects XR content 527 from the content library 525 based on one or more user inputs 521 (e.g., a voice command, a selection from a menu of XR content items, and/or the like).

In various implementations, the content manager 530 manages and updates the layout, setup, structure, and/or the like for the XR environment 128, including one or more of VAs, XR content, one or more UI elements associated with the XR content, and/or the like, based on the characterization vector 419, (optionally) the user inputs 521, and/or the like. To that end, the content manager 530 includes the frame buffer 532, the content updater 534, and the feedback engine 536.

In some implementations, the frame buffer 532 includes XR content, a rendered image frame, and/or the like for one or more past instances and/or frames. In some implementations, the content updater 534 modifies the XR environment 128 over time based on the characterization vector 419, the tiered posture awareness feedback 469, the user inputs 521 associated with modifying and/or manipulating the XR content or VA(s), translational or rotational movement of objects within the physical environment 105, translational or rotational movement of the electronic device 120 (or the user 150), and/or the like. In some implementations, the feedback engine 536 generates sensory feedback (e.g., visual feedback such as text or lighting changes, audio feedback, haptic feedback, etc.) associated with the XR environment 128.

According to some implementations, the pose determiner 552 determines a current camera pose of the electronic device 120 and/or the user 150 relative to the XR environment 128 and/or the physical environment 105 based at least in part on the pose characterization vector 415. In some implementations, the renderer 554 renders the VA(s), the XR content 527, one or more UI elements associated with the XR content, and/or the like according to the current camera pose relative thereto.

According to some implementations, the optional image processing architecture 556 obtains an image stream from an image capture device 370 including one or more images of the physical environment 105 from the current camera pose of the electronic device 120 and/or the user 150. In some implementations, the image processing architecture 556 also performs one or more image processing operations on the image stream such as warping, color correction, gamma correction, sharpening, noise reduction, white balance, and/or the like. In some implementations, the optional compositor 558 composites the rendered XR content with the processed image stream of the physical environment 105 from the image processing architecture 556 to produce rendered image frames of the XR environment 128. In various implementations, the presenter 560 presents the rendered image frames of the XR environment 128 to the user 150 via the one or more displays 312. One of ordinary skill in the art will appreciate that the optional image processing architecture 556 and the optional compositor 558 may not be applicable for fully virtual environments (or optical see-through scenarios).

FIGS. 6A-6J illustrate a plurality of three-dimensional (3D) environments associated with tiered posture awareness in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, the plurality of interfaces is rendered and presented by a computing system such as the controller 110 shown in FIGS. 1 and 2; the electronic device 120 shown in FIGS. 1 and 3; and/or a suitable combination thereof.

In some implementations, the plurality of 3D environments in FIGS. 6A-6J correspond to the XR environment 128 shown in FIG. 1 (e.g., a 3D or volumetric user interface). As such, according to some implementations, the electronic device 120 presents the plurality of 3D environments to the user 150 while the user 150 is physically present within a physical environment, which is currently within the FOV 111 of an exterior-facing image sensor of the electronic device 120 (e.g., as shown in FIG. 1). In other words, in some implementations, the electronic device 120 is configured to present XR content (e.g., virtual content) and to enable optical see-through or video pass-through of at least a portion of the physical environment on the display 122. For example, the electronic device 120 corresponds to a mobile phone, tablet, laptop, near-eye system, wearable computing device, or the like. As such, in some implementations, the user 150 holds the electronic device 120 in their hand(s) similar to the operating environment 100 in FIG. 1.

Figure 6A:
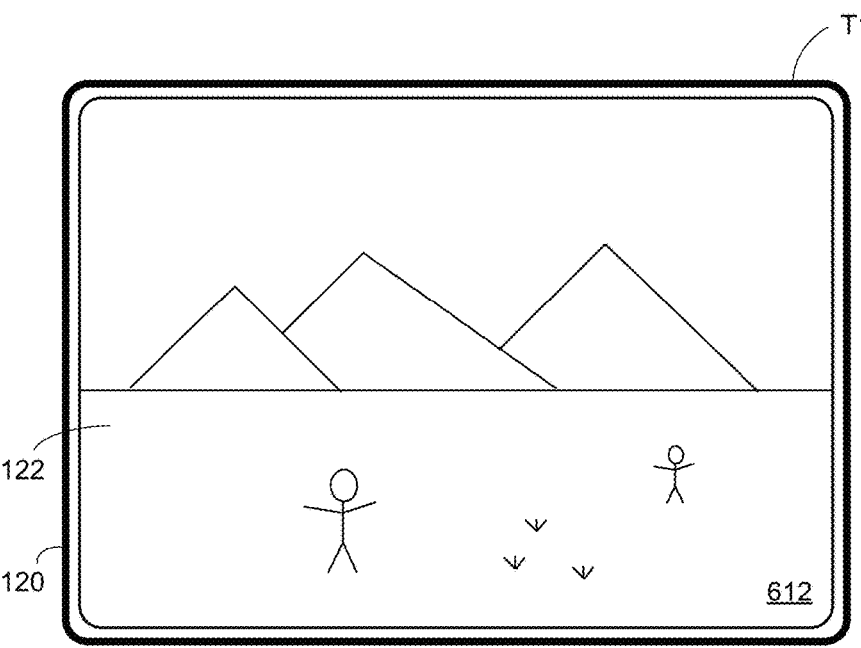
FIGS. 6A-6J illustrate a plurality of 3D environments associated with tiered posture awareness in accordance with some implementations.

As shown in FIG. 6A, the electronic device 120 presents a 3D environment 612 on the display 122 at time T1. Continuing with this example, while presenting the 3D environment 612, the electronic device 120 obtains a notification 613 for presentation within the 3D environment 612 such as an email, a text message, a social media message, an electronic message, an operating system message, or the like. In response to obtaining the notification 613, the electronic device 120 determines a current accumulated strain value 614 for the user of the electronic device 120 based on at least one of head pose information or body pose information (or change(s) thereto) for the user of the electronic device 120.

Figure 6B:
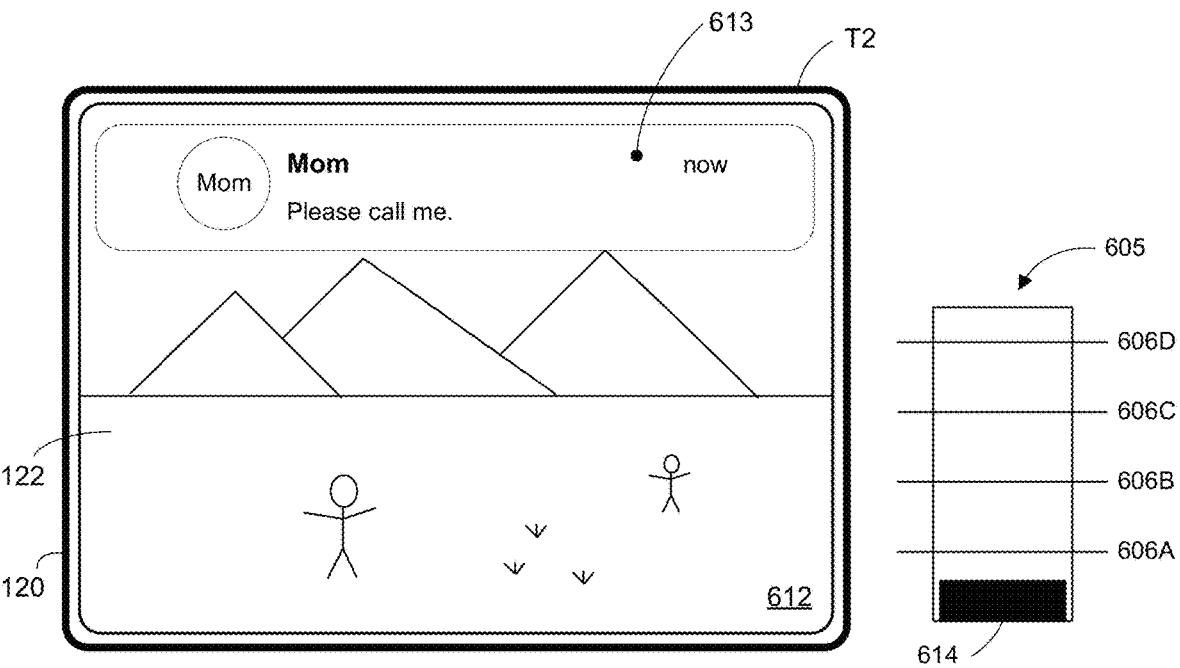

According to some implementations, FIG. 6B illustrates a representation 605 of the accumulated strain of the user of the electronic device 120 with the current accumulated strain value 614. The representation 605 of the accumulated strain of the user of the electronic device 120 also shows a first posture awareness threshold 606A, a second posture awareness threshold 606B, a third posture awareness threshold 606C, and a fourth posture awareness threshold 606D. One of ordinary skill in the art will appreciate that the representation 605 of the accumulated strain of the user of the electronic device 120 may or may not be presented on the display 122. One of ordinary skill in the art will further appreciate that the representation 605 of the accumulated strain of the user of the electronic device 120 may be presented in various forms.

As shown in FIG. 6B, in response to obtaining the notification 613 and in accordance with a determination that the current accumulated strain value 614 for the user of the electronic device 120 does not exceed the first posture awareness threshold 606A, the electronic device 120 presents, via the display 122, the notification 613 overlaid on the 3D environment 612 at time T2. For example, the electronic device 120 presents the notification 613 at a default location or in a default manner in FIG. 6B (e.g., a pop-up notification centered within the display 122, a banner notification adjacent to the top edge of the display 122, or the like).

Figure 6C:
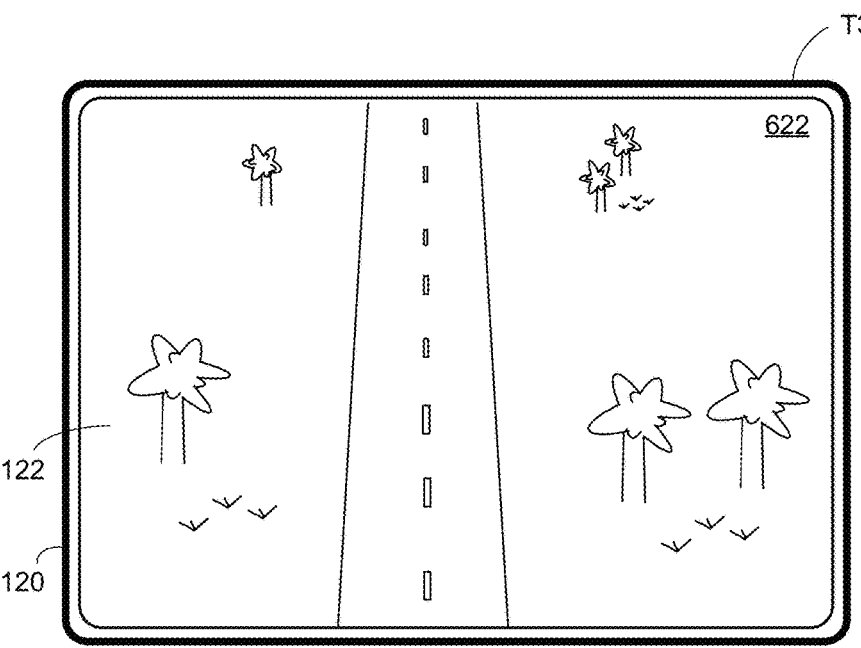

As shown in FIG. 6C, the electronic device 120 presents a 3D environment 622 on the display 122 at time T3. Continuing with this example, while presenting the 3D environment 622, the electronic device 120 obtains a notification 623 for presentation within the 3D environment 622 such as an email, a text message, a social media message, an electronic message, an operating system message, or the like. In response to obtaining the notification 623, the electronic device 120 determines a current accumulated strain value 624 for the user of the electronic device 120 based on at least one of head pose information or body pose information (or change(s) thereto) for the user of the electronic device 120.

Figure 6D:
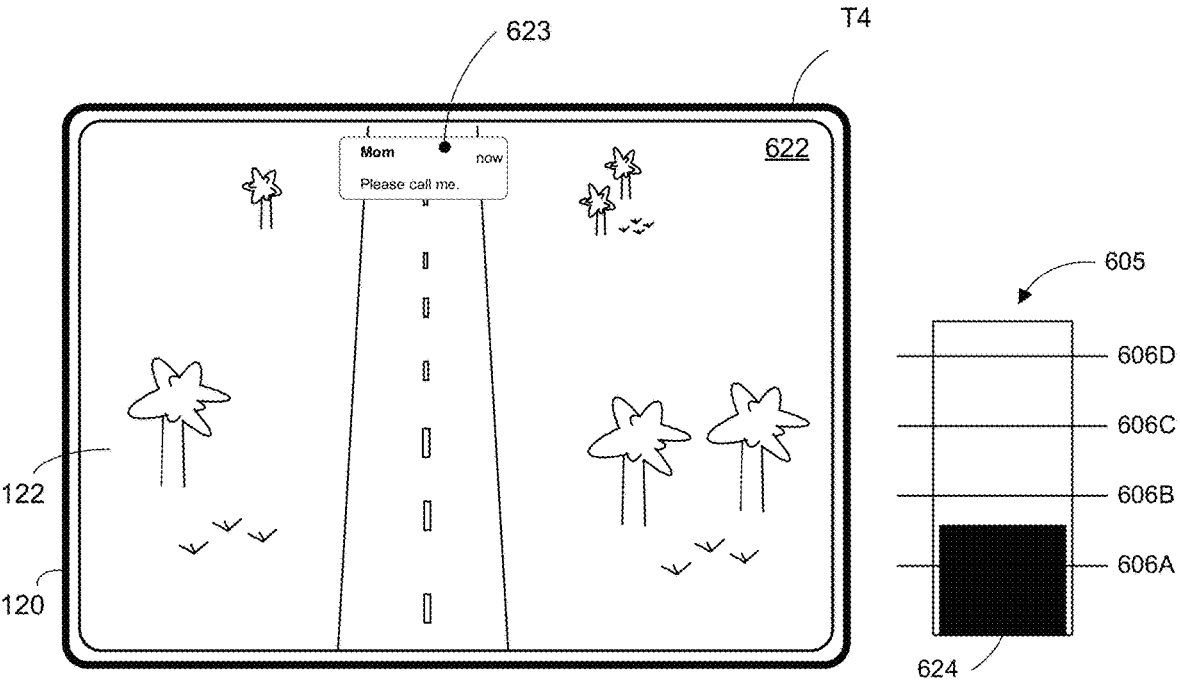

In response to obtaining the notification 623 and in accordance with a determination that the current accumulated strain value 624 for the user of the electronic device 120 exceeds the first posture awareness threshold 606A, the electronic device 120 determines a location for the notification 623 based on a height value associated with the electronic device 120 or a user of the electronic device 120 and a depth value associated with the 3D environment 622. As shown in FIG. 6D, in response to obtaining the notification 623 and in accordance with the determination that the current accumulated strain value 624 for the user of the electronic device 120 exceeds the first posture awareness threshold 606A, the electronic device 120 presents, via the display, the notification 623 at the determined location within the 3D environment 622 at time T4.

Figure 6E:
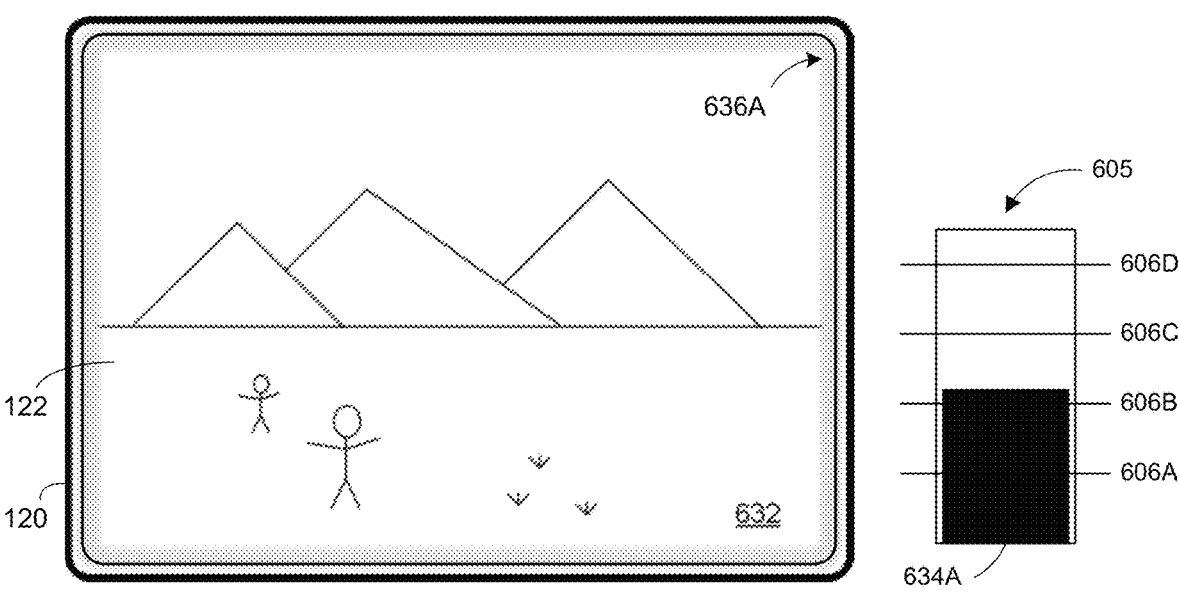
Figure 6F:
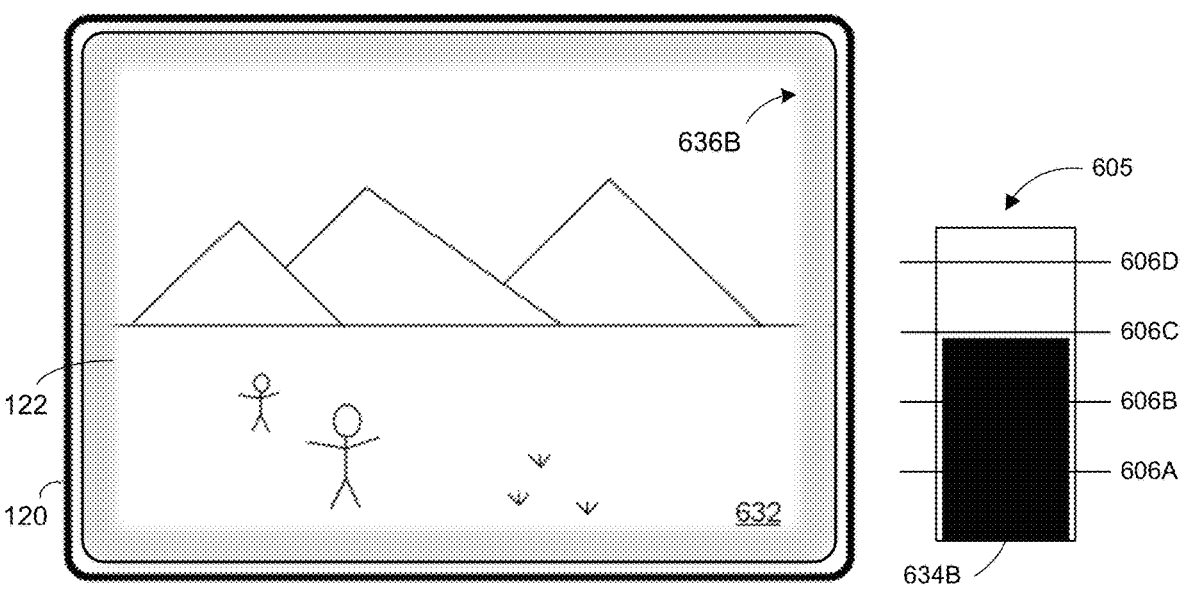

As shown in FIG. 6E, in accordance with a determination that a current accumulated strain value 634A exceeds the second posture awareness threshold 606B, the electronic device 120 presents, via the display 122, a first peripheral lighting or glow effect 636A based on the current accumulated strain value 634A while presenting a 3D environment 632. As shown in FIG. 6F, in accordance with a determination that a current accumulated strain value 634B (greater than the accumulated strain value 634A) exceeds the second posture awareness threshold 606B, the electronic device 120 presents a second peripheral lighting or glow effect 636B based on the current accumulated strain value 634B while presenting the 3D environment 632. For example, the thickness or brightness of the second peripheral lighting or glow effect 636B is greater than the first peripheral lighting or glow effect 636A because the accumulated strain value 634B in FIG. 6F is greater than the accumulated strain value 634A in FIG. 6E.

According to some implementations, one or more attributes of the peripheral lighting or glow effect (e.g., the thickness, brightness, wavelength, and/or the like) are based on the magnitude of the current accumulated strain value. As such, in one example, a brightness value of the peripheral lighting effect increases as the accumulated neck strain increases, and the brightness value of the peripheral lighting effect decreases as the accumulated neck strain decreases. As another example, a wavelength of the peripheral lighting effect increases as the accumulated neck strain increases (e.g., green to red), and the wavelength of the peripheral lighting effect decreases as the accumulated neck strain decreases (e.g., red to green). As yet another example, a thickness or brightness value of the peripheral glow effect increases as the accumulated neck strain increases, and the thickness or brightness value of the peripheral glow effect decreases as the accumulated neck strain decreases.

Figure 6G:
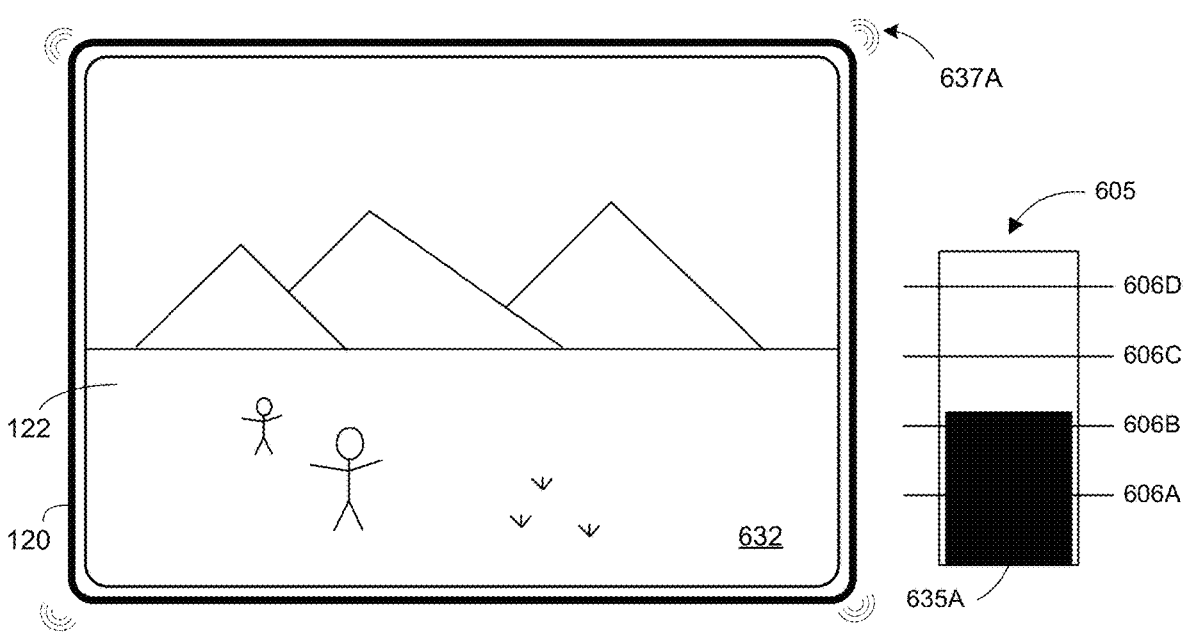
Figure 6H:
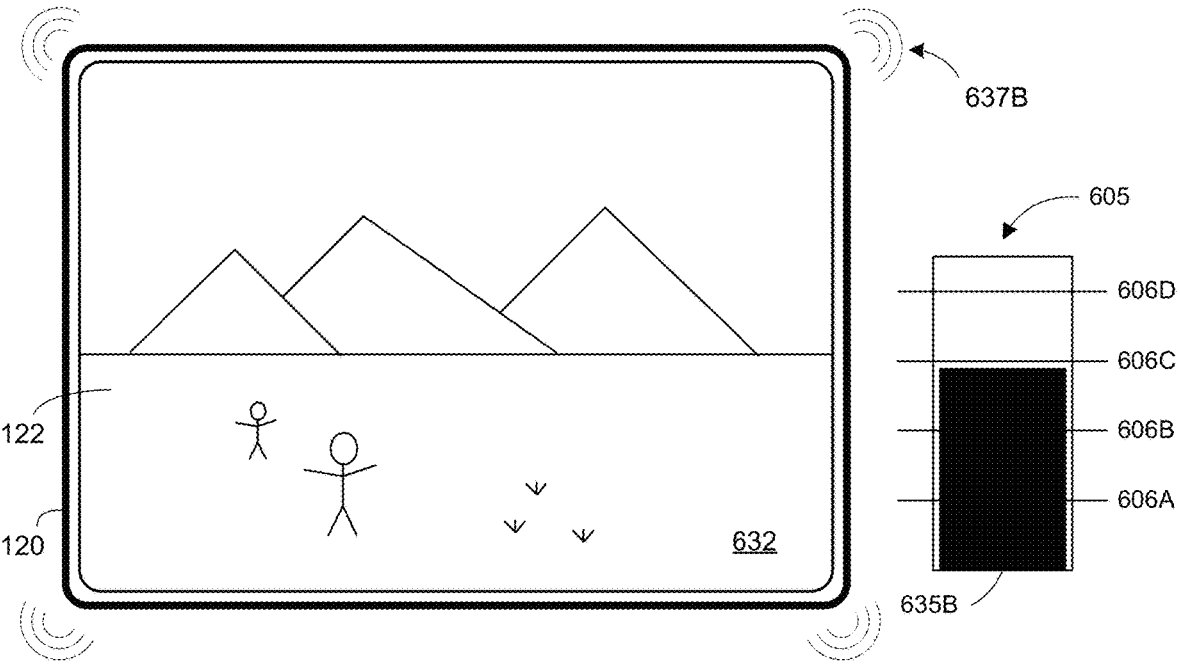

As shown in FIG. 6G, in accordance with a determination that a current accumulated strain value 635A exceeds the second posture awareness threshold 606B, the electronic device 120 provides a first spatial audio effect 637A based on the current accumulated strain value 635A while presenting the 3D environment 632. As shown in FIG. 6H, in accordance with a determination that a current accumulated strain value 635B (greater than the accumulated strain value 635A) exceeds the second posture awareness threshold 606B, the electronic device 120 provides a second spatial audio effect 637B based on the current accumulated strain value 635B while presenting the 3D environment 632. As one example, the volume of the second spatial audio effect 637B is greater than the first spatial audio effect 637A because the accumulated strain value 634B is greater than the accumulated strain value 634A. As another example, the distance of the second spatial audio effect 637B is closer relative to the user than the first spatial audio effect 637A because the accumulated strain value 634B in FIG. 6H is greater than the accumulated strain value 634A in FIG. 6G.

According to some implementations, one or more attributes of the spatial audio effect (e.g., the volume, the distance relative to the user, and/or the like) are based on the magnitude of the current accumulated strain value. As such, in one example, a volume of the spatial audio effect increases as the accumulated neck strain increases, and the volume of the spatial audio effect decreases as the accumulated neck strain decreases. As another example, a distance of the spatial audio effect decreases relative to the user as the accumulated neck strain increases, and the distance of the spatial audio effect increases relative to the user as the accumulated neck strain decreases.

In some implementations, a location of the spatial audio effect may be determined based on a height value associated with the electronic device 120 or the user of the electronic device 120. For example, the spatial audio effect may be positioned at vanishing point associated with the 3D environment or a point on a horizon within the 3D environment relative to a sightline of the user. In some implementations, the visual and audio effects presented in accordance with a determination that a current accumulated strain value exceeds the second posture awareness threshold 606B may be presented without the electronic device 120 first obtaining a notification.

Figure 6I:
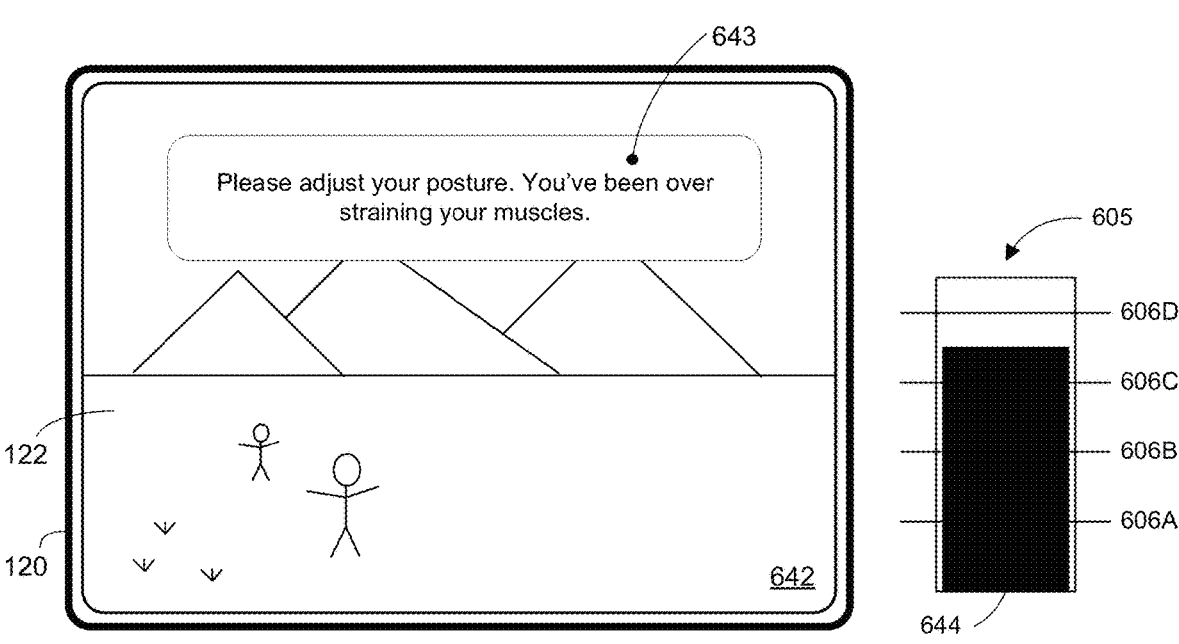

As shown in FIG. 6I, in accordance with a determination that a current accumulated strain value 644 exceeds the third posture awareness threshold 606C, the electronic device 120 presents, via the display 122, an alert notification 643 indicating that the user has been overstraining their muscles while presenting a 3D environment 642. In some implementations, the electronic device 120 presents the alert notification 643 at a default location or in a default manner within the 3D environment 642 (e.g., a pop-up notification centered within the display 122, a banner notification adjacent to the top edge of the display 122, or the like). In some implementations, the electronic device 120 presents the alert notification 643 based on a height value associated with the electronic device 120 or the user of the electronic device 120 and a depth value associated with the 3D environment 642.

Figure 6J:
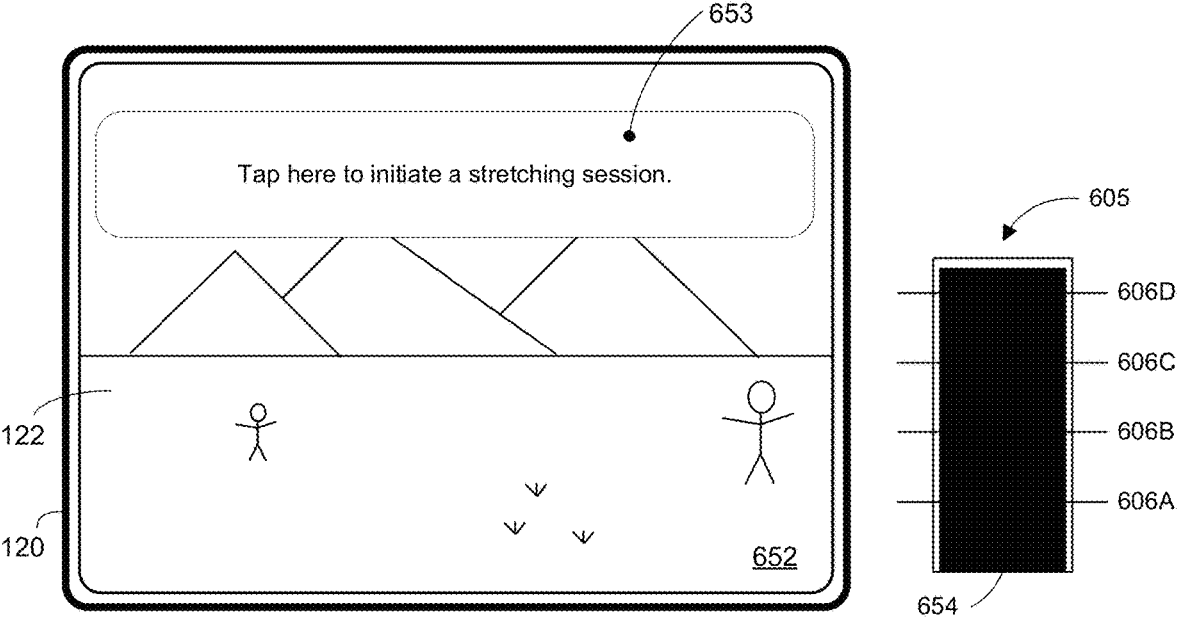

As shown in FIG. 6J, in accordance with a determination that a current accumulated strain value 654 exceeds the fourth posture awareness threshold 606D, the electronic device 120 presents, via the display 122, an affordance 653 while presenting a 3D environment 652, wherein the affordance 653 enables the user to initiate a stretching session to ameliorate the accumulated strain value. In some implementations, the electronic device 120 presents the affordance 653 at a default location or in a default manner within the 3D environment 652 (e.g., a pop-up notification centered within the display 122, a banner notification adjacent to the top edge of the display 122, or the like). In some implementations, the electronic device 120 presents the affordance 653 based on a height value associated with the electronic device 120 or the user of the electronic device 120 and a depth value associated with the 3D environment 652.

FIGS. 7A-7C illustrate a flowchart representation of a method 700 of tiered posture awareness with some implementations. In various implementations, the method 700 is performed at a computing system including non-transitory memory and one or more processors, wherein the computing system is communicatively coupled to a display device and one or more input devices (e.g., the electronic device 120 shown in FIGS. 1 and 3; the controller 110 in FIGS. 1 and 2; or a suitable combination thereof). In some implementations, the method 700 is performed by processing logic, including hardware, firmware, software, or a combination thereof. In some implementations, the method 700 is performed by a processor executing code stored in a non-transitory computer-readable medium (e.g., a memory). In some implementations, the computing system corresponds to one of a tablet, a laptop, a mobile phone, a near-eye system, a wearable computing device, or the like. In some implementations, the one or more input devices correspond to a computer vision (CV) engine that uses an image stream from one or more exterior-facing image sensors, a finger/hand/extremity tracking engine, an eye tracking engine, a touch-sensitive surface, one or more microphones, and/or the like.

As discussed above, many persons (e.g., the user 150 in FIG. 1) may spend a significant number of hours at their computers or other devices during both work and non-work hours. This time spent using a computer or other devices may negatively impact the posture of said person. As such, described herein is a method and device for promoting posture awareness via a tiered posture awareness scheme based on an accumulated strain value for the user.

As represented by block 702, while presenting a three-dimensional (3D) environment via the display device, the method 700 includes obtaining (e.g., receiving, retrieving, determining/generating, etc.) head pose information for a user associated with the computing system. As one example, with reference to FIG. 6A, the electronic device 120 presents a 3D environment 612 on the display 122 at time T1. As another example, with reference to FIG. 6C, the electronic device 120 presents a 3D environment 622 on the display 122 at time T3. In some implementations, the 3D environment corresponds to a representation of a physical environment, an XR environment, or the like. For example, with reference to FIG. 5, the computing system or a portion thereof (e.g., the rendering engine 550) renders one or more image frames for an XR environment 128 (e.g., the 3D environment), and the computing system or a portion thereof (e.g., the presenter 560) presents the rendered image frames for the XR environment 128 to the user 150 via the one or more displays 312.

In some implementations, the display device corresponds to a transparent lens assembly, and wherein presenting the 3D environment includes projecting at least a portion of the 3D environment onto the transparent lens assembly. In some implementations, the display device corresponds to a near-eye system, and wherein presenting the 3D environment includes compositing at least a portion of the 3D environment with one or more images of a physical environment captured by an exterior-facing image sensor.

In some implementations, the head pose information at least includes 3DOF rotational values. For example, with reference to FIGS. 4A and 4B, the computing system or a portion thereof (e.g., the head/body pose tracking engine 414) obtains (e.g., receives, retrieves, or detects/determines/generates) a pose characterization vector 415 based on the input data and update the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like.

As represented by block 704, the method 700 includes determining an accumulated strain value for the user based on the head pose information. In some implementations, the computing system updates the accumulated strain value over time according to a determination that a change to the head pose information exceeds a deterministic or non-deterministic significance threshold to filter out noise or small movements. For example, the change to the head pose information corresponds to a change to the position or orientation of the head pose.

For example, with reference to FIG. 4C, the computing system or a portion thereof (e.g., the head/body/neck mechanics engine 462) obtains (e.g., receives, retrieves, or determines/generates) displacement, velocity, acceleration, jerk, torque, etc. values for the head/body/neck of the user 150 based on changes to the pose characterization vector 415. With continued reference to FIG. 4C, the computing system or a portion thereof (e.g., the strain analyzer 464) determines current strain information 480 for one or more muscles or muscle groups based on: the displacement, velocity, acceleration, jerk, torque, etc. values for the head/body/neck of the user 150 from the head/body/neck mechanics engine 462; historical information 466; and the context information vector 470. In some implementations, the strain analyzer 464 determines the current strain information 480 based on strain increase logic 465A and/or strain decrease logic 465B. As shown in FIG. 4D, the current strain information 480 includes accumulated strain information 486: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information.

In some implementations, as represented by block 706, while presenting the 3D environment via the display device, the method 700 includes obtaining (e.g., receiving, retrieving, determining/generating, etc.) body pose information for the user associated with the computing system, wherein determining the accumulated strain value for the user is based on the head pose information and the body pose information. In some implementations, the computing system updates the accumulated strain value over time according to a determination that a change to the body pose information exceeds a deterministic or non-deterministic significance threshold to filter out noise or small movements. For example, the change to the body pose information corresponds to a change to the position or orientation of the body pose.

In some implementations, the body pose information at least includes 3DOF rotational values. For example, with reference to FIGS. 4A and 4B, the computing system or a portion thereof (e.g., the head/body pose tracking engine 414) obtains (e.g., receives, retrieves, or detects/determines/generates) a pose characterization vector 415 based on the input data and updates the pose characterization vector 415 over time. For example, as shown in FIG. 4B, the pose characterization vector 415 includes a head pose descriptor 442A (e.g., upward, downward, neutral, etc.), translational values 442B for the head pose, rotational values 442C for the head pose, a body pose descriptor 444A (e.g., standing, sitting, prone, etc.), translational values 444B for body sections/extremities/limbs/joints, rotational values 444C for the body sections/extremities/limbs/joints, and/or the like.

In some implementations, the method 700 includes updating the accumulated strain value for the user over time based on a change to the head pose information by increasing the accumulated strain value according to a determination that the change to the head pose information causes increased strain to a specific muscle or muscle group of the user. In some implementations, if the computing system obtains the body pose information for the user, the accumulated strain increase logic may also factor in a change to the body pose information. In some implementations, the method 700 includes updating the accumulated strain value for the user over time based on a change to the head pose information by decreasing the accumulated strain value according to a determination that the change to the head pose information causes decreased strain to a specific muscle or muscle group of the user. In some implementations, if the computing system obtains the body pose information for the user, the accumulated strain decrease logic may also factor in a change to the body pose information.

For example, with reference to FIG. 4C, the computing system or a portion thereof (e.g., the head/body/neck mechanics engine 462) obtains (e.g., receives, retrieves, or determines/generates) displacement, velocity, acceleration, jerk, torque, etc. values for the head/body/neck of the user 150 based on changes to the pose characterization vector 415. With continued reference to FIG. 4C, the computing system or a portion thereof (e.g., the strain analyzer 464) determines current strain information 480 for one or more muscles or muscle groups based on: the displacement, velocity, acceleration, jerk, torque, etc. values for the head/body/neck of the user 150 from the head/body/neck mechanics engine 462; historical information 466; and the context information vector 470. In some implementations, the strain analyzer 464 determines the current strain information 480 based on the strain increase logic 465A and/or the strain decrease logic 465B.

In some implementations, as represented by block 708, the accumulated strain value is based on a plurality of strain values for a plurality of muscles or muscle groups of the user. In some implementations, the accumulated strain value is a function of the plurality of strain values for the plurality of muscles or muscle groups of the user. For example, some muscles or muscle groups may be weighted differently based on user preferences, user history, or the like. As shown in FIG. 4D, the current strain information 480 includes accumulated strain information 486 with: a current accumulated strain value 489A associated with a function of one or more of the current muscle strain values 485A, 485B, 485C, 485D, and 485E for muscles or muscle groups/regions 484A, 484B, 484C, 484D, and 484E, respectively, of the user 150; a pointer to historical accumulated strain information 489B within the historical information 466; and miscellaneous information 489C associated with the accumulated strain information.

In some implementations, as represented by block 710, the method 700 includes: obtaining (e.g., receiving, retrieving, detecting, etc.) a notification for presentation, wherein the virtual content corresponds to the notification; and in response to obtaining the notification for presentation, determining whether the accumulated strain value for the user exceeds the first posture awareness threshold. In some implementations, the trigger for determining whether the accumulated strain value for the user exceeds the first posture awareness threshold corresponds to reception/detection of the notification. As one example, with reference to the sequence in FIGS. 6A and 6B, in response to obtaining the notification 613, the electronic device 120 determines a current accumulated strain value 614 for the user of the electronic device 120 based on at least one of head pose information or body pose information (or change(s) thereto) for the user of the electronic device 120. As another example, with reference to the sequence in FIGS. 6C and 6D, in response to obtaining the notification 623, the electronic device 120 determines a current accumulated strain value 624 for the user of the electronic device 120 based on at least one of head pose information or body pose information (or change(s) thereto) for the user of the electronic device 120.

In some implementations, the notification corresponds to one of: a notification associated with an operating system of the computing system, a new or unread notification associated with a foreground application or program, a new or unread notification associated with a background application or program, a new or unread electronic mail (email) notification, a new or unread short message service (SMS) notification, a new or unread media message service (MMS) notification, or a new or unread social media notification. As one example, with reference to the sequence in FIGS. 6A and 6B, the notification 613 corresponds to a text message or SMS notification. As another example, with reference to the sequence in FIGS. 6C and 6D, the notification 623 corresponds to a text message or SMS notification.

In some implementations, in response to obtaining the notification for presentation and in accordance with a determination that the accumulated strain value for the user does not exceed the first posture awareness threshold, the method 700 includes maintaining presentation of the 3D environment and presenting the notification at a default location. In some implementations, the notification is presented at a default location within the 3D environment. In some implementations, the notification is presented at a default location such as at predefined x, y pixel coordinates of the display or predefined x, y, z coordinates relative to the field-of-view of the user.

For example, with reference to the sequence in FIGS. 6A and 6B, in response to obtaining the notification 613 and in accordance with a determination that the current accumulated strain value 614 for the user of the electronic device 120 does not exceed the first posture awareness threshold 606A, the electronic device 120 presents, via the display 122, the notification 613 overlaid on the 3D environment 612 at time T2. For example, the electronic device 120 presents the notification 613 at a default location or in a default manner in FIG. 6B (e.g., a pop-up notification centered within the display 122, a banner notification adjacent to the top edge of the display 122, or the like).

As represented by block 712, in accordance with a determination that the accumulated strain value for the user exceeds a first posture awareness threshold, the method 700 includes: determining a location for virtual content based on a height value associated with the electronic device 120 or the user and a depth value associated with the 3D environment; and presenting, via the display device, the virtual content at the determined location while continuing to present the 3D environment via the display device. In some implementations, the first posture awareness threshold corresponds to a deterministic value. In some implementations, the first posture awareness threshold corresponds to a non-deterministic value based on user-specific history information, crowd-sourced information, and/or the like. In some implementations, determining the location for virtual content and presenting the virtual content at the determined location may be performed in accordance with a determination that the accumulated strain value for the user exceeds the first posture awareness threshold, but not a second posture awareness threshold.

Presenting the virtual content as described above for block 712 advantageously encourages a healthy neck posture without being overly intrusive in response to detecting a mild amount of neck strain (e.g., corresponding to the first posture awareness threshold). In particular, by opportunistically presenting existing notifications at the determined location, the user may be encouraged to position their neck in a healthy posture without being overwhelmed with additional, dedicated notifications regarding the user's posture.

For example, with reference to the sequence in FIGS. 6C and 6D, in response to obtaining the notification 623 and in accordance with a determination that the current accumulated strain value 624 for the user of the electronic device 120 exceeds the first posture awareness threshold 606A, the electronic device 120 determines a location for the notification 623 based on a height value associated with the electronic device 120 or the user of the electronic device 120 and a depth value associated with the 3D environment 622. As shown in FIG. 6D, in response to obtaining the notification 623 and in accordance with the determination that the current accumulated strain value 624 for the user of the electronic device 120 exceeds the first posture awareness threshold 606A, the electronic device 120 presents, via the display, the notification 623 at the determined location within the 3D environment 622 at time T4.

In some implementations, the location is selected to reduce the accumulated strain value. For example, the height value corresponds to the device height, the user height, the user sightline, the focal point of the user sightline, or the like. For example, the depth value corresponds to an average depth, a mean depth, a median depth, a greatest depth, or the like for the 3D environment. In some implementations, the location is determined based on dimensions of the 3D environment, dimensions and locations of objects within the 3D environment, user profile (e.g., user height, visual acuity, etc.), user preference(s) (e.g., a preferred viewing height), body pose (e.g., sitting, standing, prone, etc., which informs height), gaze vector (e.g., height of the focal point), etc. For example, the location is selected to reduce collisions and/or occlusions with objects within the 3D environment.

For example, the virtual content corresponds to a strain alert/notification, an OS notification, an icon or badge, etc. For example, the virtual content corresponds to 2D content that is overlaid on the 3D environment at the determined location. For example, the virtual content corresponds to 3D or volumetric content that is overlaid on or composited with the 3D environment at the determined location. In some implementations, the determined location for the virtual content is updated as the head pose changes (e.g., head-locked).

In some implementations, as represented by block 714, the location for the virtual content corresponds to one of a vanishing point associated with the 3D environment or a point on a horizon within the 3D environment relative to a sightline of the user. For example, the determined location corresponds to a vanishing point or a horizon within the 3D environment relative to the user's sightline. For example, with reference to FIG. 6D, the electronic device 120 presents the notification 623 at a vanishing point within the 3D environment.

In some implementations, as represented by block 716, in accordance with a determination that the accumulated strain value for the user does not exceed the first posture awareness threshold, the method 700 includes maintaining presentation of the 3D environment and forgoing presentation of the virtual content at the determined location. In some implementations, the virtual content is presented at a default location within the 3D environment. In some implementations, the virtual content is presented at a default location such as at predefined x, y pixel coordinates of the display or predefined x, y, z coordinates relative to the field-of-view of the user.

For example, with reference to the sequence in FIGS. 6A and 6B, in response to obtaining the notification 613 and in accordance with a determination that the current accumulated strain value 614 for the user of the electronic device 120 does not exceed the first posture awareness threshold 606A, the electronic device 120 presents, via the display 122, the notification 613 overlaid on the 3D environment 612 at time T2. For example, the electronic device 120 presents the notification 613 at a default location or in a default manner in FIG. 6B (e.g., a pop-up notification centered within the display 122, a banner notification adjacent to the top edge of the display 122, or the like).

In some implementations, as represented by block 718, in accordance with a determination that the accumulated strain value for the user exceeds a second posture awareness threshold greater than the first posture awareness threshold, the method 700 includes changing an appearance of at least a portion of at least one edge of the display device. In some implementations, the second posture awareness threshold corresponds to a deterministic value. For example, the second posture awareness threshold corresponds to a non-deterministic value based on user-specific history information, crowd-sourced information, or the like. In some implementations, changing the appearance of at least a portion of at least one edge of the display device may be performed in accordance with a determination that the accumulated strain value for the user exceeds the second posture awareness threshold, but not a third posture awareness threshold.

In some implementations, as represented by block 720, changing the appearance of at least the portion of at least the one edge of the display device corresponds to peripheral lighting or a peripheral glow effect. In some implementations, the change of appearance may be coupled with haptic and/or audio feedback. In some implementations, a brightness value of the peripheral lighting increases as the accumulated neck strain increases. According to some implementations, the opposite occurs as the accumulated neck strain decreases. In some implementations, a wavelength of the peripheral lighting increases as the accumulated neck strain increases. For example, as the accumulated neck strain increases, the wavelength of the peripheral lighting changes from green to red. According to some implementations, the opposite occurs as the accumulated neck strain decreases. In some implementations, at least one of a thickness value or a brightness value of the glow effect increases as the accumulated neck strain increases. According to some implementations, the opposite occurs as the accumulated neck strain decreases.

As one example, with reference to FIG. 6E, in accordance with a determination that a current accumulated strain value 634A exceeds the second posture awareness threshold 606B, the electronic device 120 presents, via the display 122, a first peripheral lighting or glow effect 636A based on the current accumulated strain value 634A while presenting a 3D environment 632. As another example, with reference to FIG. 6F, in accordance with a determination that a current accumulated strain value 634B exceeds the second posture awareness threshold 606B, the electronic device 120 presents a second peripheral lighting or glow effect 636B based on the current accumulated strain value 634B while presenting the 3D environment 632. For example, the thickness or brightness of the second peripheral lighting or glow effect 636B is greater than the first peripheral lighting or glow effect 636A because the accumulated strain value 634B is greater than the accumulated strain value 634A.

In some implementations, as represented by block 722, in accordance with a determination that the accumulated strain value for the user exceeds a second posture awareness threshold greater than the first posture awareness threshold, the method 700 includes providing spatial audio relative to at least one auditory edge of the user. In some implementations, the computing system determines an audible range for the user based on the dimensions of a physical environment, the acoustics of the physical environment, the location of the user relative to the physical environment, the audible acuity of the user, etc. As such, the auditory edge of the user corresponds to edge of this audible range or some threshold distance relative thereto.

In some implementations, a location of the spatial audio may be determined based on a height value associated with the electronic device or the user of the electronic device. For example, the spatial audio may be positioned at vanishing point associated with the 3D environment or a point on a horizon within the 3D environment relative to a sightline of the user. In some implementations, providing spatial audio may be performed in accordance with a determination that the accumulated strain value for the user exceeds the second posture awareness threshold, but not a third posture awareness threshold.

In some implementations, a volume of the spatial audio increases as the accumulated strain value increases. According to some implementations, the opposite occurs as the accumulated strain value decreases. In some implementations, a distance of the spatial audio decreases relative to the user as the accumulated strain value increases. According to some implementations, the opposite occurs as the accumulated strain value decreases.

As one example, with reference to FIG. 6G, in accordance with a determination that a current accumulated strain value 635A exceeds the second posture awareness threshold 606B, the electronic device 120 provides a first spatial audio effect 637A based on the current accumulated strain value 635A while presenting the 3D environment 632. As one example, with reference to FIG. 6H, in accordance with a determination that a current accumulated strain value 635B exceeds the second posture awareness threshold 606B, the electronic device 120 provides a second spatial audio effect 637B based on the current accumulated strain value 635B while presenting the 3D environment 632. As one example, the volume of the second spatial audio effect 637B is greater than the first spatial audio effect 637A because the accumulated strain value 634B is greater than the accumulated strain value 634A. As another example, the distance of the second spatial audio effect 637B is closer relative to the user than the first spatial audio effect 637A because the accumulated strain value 634B is greater than the accumulated strain value 634A.

Presenting the visual or audio content as described above for blocks 720 and 722 advantageously notifies the user of a moderate amount of neck strain (e.g., corresponding to the second posture awareness threshold) in a timely, yet unobtrusive manner. In particular, the user may be notified of potential neck strain in a timely manner (e.g., without having to wait for a notification as in block 712) using subtle audio content or subtle visual content positioned toward the periphery of the user's field of view.

In some implementations, as represented by block 724, in accordance with a determination that the accumulated strain value for the user exceeds a third posture awareness threshold greater than the second posture awareness threshold, the method 700 includes presenting, via the display device, second virtual content within the 3D environment, wherein the second virtual content corresponds to an alert notification indicating that the user has been overstraining one or more muscles or muscle groups. In some implementations, the third second posture awareness threshold corresponds to a deterministic value. For example, the third posture awareness threshold corresponds to a non-deterministic value based on user-specific history information, crowd-sourced information, or the like. In some implementations, the second virtual content is presented in accordance with a determination that the accumulated strain value exceeds the third posture awareness threshold, but not a fourth posture awareness threshold.

As one example, with reference to FIG. 6I, in accordance with a determination that a current accumulated strain value 644 exceeds the third posture awareness threshold 606C, the electronic device 120 presents, via the display 122, an alert notification 643 indicating that the user has been overstraining their muscles while presenting a 3D environment 642. In some implementations, the electronic device 120 presents the alert notification 643 at a default location or in a default manner within the 3D environment 642 (e.g., a pop-up notification centered within the display 122, a banner notification adjacent to the top edge of the display 122, or the like). In some implementations, the electronic device 120 presents the alert notification 643 based on a height value associated with the electronic device 120 or the user of the electronic device 120 and a depth value associated with the 3D environment 642.

Presenting the second virtual content as described for block 724 advantageously notifies the user of a heightened amount of neck strain (e.g., corresponding to the third posture awareness threshold) in a timely and noticeable manner. In particular, the user may be notified of potential neck strain in a timely manner (e.g., without having to wait for a notification as in block 712) using second virtual content positioned in a way so as to be noticed by the user.

In some implementations, as represented by block 726, in accordance with a determination that the accumulated strain value for the user exceeds a fourth posture awareness threshold greater than the third posture awareness threshold, the method 700 includes presenting, via the display device, an affordance within the 3D environment, wherein the affordance enables the user to initiate a stretching session to ameliorate the accumulated strain value. In some implementations, the fourth posture awareness threshold corresponds to a deterministic value. For example, the fourth posture awareness threshold corresponds to a non-deterministic value based on user-specific history information, crowd-sourced information, or the like. For example, the computing system may present the stretching session based on U.S. Non-Provisional patent application Ser. No. 18/200,542, filed on May 22, 2023, which is incorporated by reference in its entirety.

As one example, with reference to FIG. 6J, in accordance with a determination that a current accumulated strain value 654 exceeds the fourth posture awareness threshold 606D, the electronic device 120 presents, via the display 122, an affordance 653 while presenting a 3D environment 652, wherein the affordance 653 enables the user to initiate a stretching session to ameliorate the accumulated strain value. In some implementations, the electronic device 120 presents the affordance 653 at a default location or in a default manner within the 3D environment 652 (e.g., a pop-up notification centered within the display 122, a banner notification adjacent to the top edge of the display 122, or the like). In some implementations, the electronic device 120 presents the affordance 653 based on a height value associated with the electronic device 120 or the user of the electronic device 120 and a depth value associated with the 3D environment 652.

Presenting the affordance as described above for block 726 advantageously provides the user with a simple way to initiate a stretching session to ameliorate a high amount of neck strain (e.g., corresponding to the fourth posture awareness threshold). In particular, since the user may be experiencing an undesirably high amount of neck strain, it may be beneficial for the user to perform a neck stretch in a timely manner. Providing an affordance to perform the neck stretch reduces the time and effort required by the user to initiate the stretching session.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first media item could be termed a second media item, and, similarly, a second media item could be termed a first media item, which changing the meaning of the description, so long as the occurrences of the "first media item" are renamed consistently and the occurrences of the "second media item" are renamed consistently. The first media item and the second media item are both media items, but they are not the same media item.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:

at a computing system including non-transitory memory and one or more processors, wherein the computing system is communicatively coupled to a display device and one or more input devices via a communication interface:

while presenting a three-dimensional (3D) environment, via the display device, obtaining head pose information for a user associated with the computing system;

determining an accumulated strain value for the user based on the head pose information, wherein the accumulated strain value is updated over time for the user based on movements of the user; and in accordance with a determination that the accumulated strain value for the user exceeds a first posture awareness threshold:

determining a location for virtual content based on a height value associated with the user and a depth value associated with the 3D environment; and presenting, via the display device, the virtual content at the determined location while continuing to present the 3D environment via the display device.

2. The method of claim 1, wherein the location for the virtual content corresponds to one of a vanishing point associated with the 3D environment or a point on a horizon within the 3D environment relative to a sightline of the user.

3. The method of claim 1, further comprising:

while presenting the 3D environment via the display device, obtaining body pose information for the user associated with the computing system, wherein determining the accumulated strain value for the user is based on the head pose information and the body pose information.

4. The method of claim 1, further comprising:

obtaining a notification for presentation, wherein the virtual content corresponds to the notification; and in response to obtaining the notification for presentation, determining whether the accumulated strain value for the user exceeds the first posture awareness threshold.

5. The method of claim 4, wherein the notification corresponds to one of: a notification associated with an operating system of the computing system, a new or unread notification associated with a foreground application or program, a new or unread notification associated with a background application or program, a new or unread electronic mail (email) notification, a new or unread short message service (SMS) notification, a new or unread media message service (MMS) notification, or a new or unread social media notification.

6. The method of claim 4, further comprising:

in accordance with a determination that the accumulated strain value for the user does not exceed the first posture awareness threshold, maintaining presentation of the 3D environment and presenting the notification at a default location.

7. The method of claim 1, further comprising:

in accordance with a determination that the accumulated strain value for the user does not exceed the first posture awareness threshold, maintaining presentation of the 3D environment and forgoing presentation of the virtual content at the determined location.

8. The method of claim 1, wherein the accumulated strain value is based on a plurality of strain values for a plurality of muscles or muscle groups of the user.

9. The method of claim 1, further comprising:

updating the accumulated strain value for the user over time based on a change to the head pose information by increasing the accumulated strain value according to a determination that the change to the head pose information causes increased strain to a specific muscle or muscle group of the user.

10. The method of claim 1, further comprising:

updating the accumulated strain value for the user over time based on a change to the head pose information by decreasing the accumulated strain value according to a determination that the change to the head pose information causes decreased strain to a specific muscle or muscle group of the user.

11. The method of claim 1, further comprising:

in accordance with a determination that the accumulated strain value for the user exceeds a second posture awareness threshold greater than the first posture awareness threshold, changing an appearance of at least a portion of at least one edge of the display device.

12. The method of claim 11, wherein changing the appearance of at least the portion of at least the one edge of the display device corresponds to peripheral lighting or a peripheral glow effect.

13. The method of claim 12, wherein a brightness value of the peripheral lighting increases as the accumulated strain value increases, and wherein a wavelength of the peripheral lighting increases as the accumulated strain value increases.

14. The method of claim 12 wherein at least one of a thickness value or a brightness value of the peripheral glow effect increases as the accumulated strain value increases.

15. The method of claim 11, further comprising:

in accordance with a determination that the accumulated strain value for the user exceeds the second posture awareness threshold greater than the first posture awareness threshold, providing spatial audio relative to at least one auditory edge of the user.

16. The method of claim 15, wherein a volume of the spatial audio increases as the accumulated strain value increases, and wherein a distance of the spatial audio decreases relative to the user as the accumulated strain value increases.

17. The method of claim 11, further comprising:

in accordance with a determination that the accumulated strain value for the user exceeds a third posture aware- ness threshold greater than the second posture awareness threshold, presenting, via the display device, sec- ond virtual content within the 3D environment, wherein the second virtual content corresponds to an alert notification indicating that the user has been overstrain- ing one or more muscles or muscle groups.

18. The method of claim 17, further comprising:

in accordance with a determination that the accumulated strain value for the user exceeds a fourth posture awareness threshold greater than the third posture awareness threshold, presenting, via the display device, an affordance within the 3D environment, wherein the affordance enables the user to initiate a stretching session to ameliorate the accumulated strain value.

19. A device comprising:

one or more processors;

a non-transitory memory;

an interface for communicating with a display device and one or more input devices; and one or more programs stored in the non-transitory memory, which, when executed by the one or more processors, cause the device to:

while presenting a three-dimensional (3D) environ- ment, via the display device, obtain head pose infor- mation for a user associated with the device;

determine an accumulated strain value for the user based on the head pose information, wherein the accumulated strain value is updated over time for the user based on movements of the user; and in accordance with a determination that the accumu- lated strain value for the user exceeds a first posture awareness threshold:

determine a location for virtual content based on a height value associated with the user and a depth value associated with the 3D environment; and present, via the display device, the virtual content at the determined location while continuing to pres- ent the 3D environment via the display device.

20. A non-transitory memory storing one or more pro- grams, which, when executed by one or more processors of a device with an interface for communicating with a display device and one or more input devices, cause the device to:

while presenting a three-dimensional (3D) environment, via the display device, obtain head pose information for a user associated with the device;

determine an accumulated strain value for the user based on the head pose information, wherein the accumulated strain value is updated over time for the user based on movements of the user; and in accordance with a determination that the accumulated strain value for the user exceeds a first posture aware- ness threshold:

determine a location for virtual content based on a height value associated with the user and a depth value associated with the 3D environment; and present, via the display device, the virtual content at the determined location while continuing to present the 3D environment via the display device.

* * * * *